United States Patent
Hilsdale et al.

(10) Patent No.: US 9,953,041 B2
(45) Date of Patent: Apr. 24, 2018

(54) LONG-TERM DATA STORAGE SERVICE FOR WEARABLE DEVICE DATA

(71) Applicant: Verily Life Sciences LLC, Mountain View, CA (US)

(72) Inventors: Erik Hilsdale, Sunnyvale, CA (US); Brian Taewon Park, San Francisco, CA (US); David Andrew Gibson, Mountain View, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 507 days.

(21) Appl. No.: 14/484,862

(22) Filed: Sep. 12, 2014

(65) Prior Publication Data

US 2016/0078061 A1    Mar. 17, 2016

(51) Int. Cl.
*G06F 7/00*    (2006.01)
*G06F 17/30*    (2006.01)
*G06F 19/00*    (2018.01)

(52) U.S. Cl.
CPC .. *G06F 17/30289* (2013.01); *G06F 17/30371* (2013.01); *G06F 19/322* (2013.01); *G06F 19/3406* (2013.01); *G06F 19/3418* (2013.01)

(58) Field of Classification Search
CPC ......... G06F 17/30289; G06F 17/30371; G06F 19/322; G06F 19/3406; G06F 19/3418
See application file for complete search history.

(56) References Cited

U.S. PATENT DOCUMENTS

| | | |
|---|---|---|
| 2003/0046228 A1 | 3/2003 | Berney |
| 2003/0212336 A1 | 11/2003 | Lee et al. |
| 2004/0152957 A1* | 8/2004 | Stivoric ............... A61B 5/01 600/300 |

(Continued)

FOREIGN PATENT DOCUMENTS

| | | |
|---|---|---|
| WO | 2012178134 A2 | 12/2012 |
| WO | 2013/096954 A1 | 6/2013 |

OTHER PUBLICATIONS

International Search Report and Written Opinion of International Application No. PCT/US2015/049364 dated Dec. 22, 2015 (dated Dec. 23, 2015).

(Continued)

*Primary Examiner* — Tuan A Pham
*Assistant Examiner* — Thai V Dang
(74) *Attorney, Agent, or Firm* — McDonnell Boehnen Hulbert & Berghoff LLP

(57) ABSTRACT

Methods and apparatus for storing data about biological entities are provided. A computing device can receive a plurality of data items about a biological entity from a plurality of sources. The computing device can verify each data item of the plurality of data items using the computing device by at least: determining a source of the data item from among the plurality of sources, determining a provenance for the data item associated with the source of the data item, and verifying that the data item is associated with the biological entity based at least on the provenance for the data item associated with the source of the data item. After verifying that a particular data item is associated with the biological entity, the computing device can store the particular data item in a data log associated with the biological entity.

12 Claims, 16 Drawing Sheets

(56) References Cited

U.S. PATENT DOCUMENTS

| | | | |
|---|---|---|---|
| 2004/0155790 A1* | 8/2004 | Tsuji | H04W 74/04 340/4.21 |
| 2007/0100666 A1* | 5/2007 | Stivoric | G01R 29/0814 705/3 |
| 2008/0191866 A1 | 8/2008 | Falck et al. | |
| 2008/0294018 A1 | 11/2008 | Kurtz et al. | |
| 2009/0240193 A1* | 9/2009 | Mensinger | A61B 5/7445 604/66 |
| 2011/0238379 A1 | 9/2011 | Misra et al. | |
| 2012/0041278 A1* | 2/2012 | Sadhu | A61B 5/0006 600/301 |
| 2012/0316455 A1* | 12/2012 | Rahman | G01C 22/006 600/547 |
| 2012/0316932 A1 | 12/2012 | Rahman et al. | |
| 2012/0317024 A1* | 12/2012 | Rahman | G06Q 30/02 705/42 |
| 2013/0285836 A1 | 10/2013 | Proud | |
| 2014/0073486 A1* | 3/2014 | Ahmed | A61B 5/02405 482/9 |
| 2014/0223462 A1* | 8/2014 | Aimone | H04N 21/42201 725/10 |
| 2014/0357995 A1* | 12/2014 | Brumfield | A61B 5/7282 600/438 |

OTHER PUBLICATIONS

Chen et al., "Wireless in loco Sensor Data Collection and Applications", Rutgers University, 2004 (6 pages).

\* cited by examiner

Example Data Format 1100

| Data-Independent Provenance 1110 |
|---|
| Data-Dependent Provenance1 1150a |
| Data Item1 1170a |
| Data-Dependent Provenance2 1150b |
| Data Item2 1170b |
| .... |

Example Data-Independent Provenance 1110

Default Values 1130

| Number of Data Items 1112 | One 1132 |
|---|---|
| Data Source 1114 | Internal 1134 |
| Time Data Received 1116 | Now 1136 |
| Data Size 1118 | <As received> 1138 |
| Data Type 1120 | Unknown 1140 |

Example Data-Dependent Provenance Fields 1150

| Data Sub-Type(s) 1152 |
|---|
| Location 1154 |
| Associated Entity ID 1156 |
| Entity Providing Data 1158 |
| Time Data Generated 1160 |
| Sensor Used to Generate Data 1162 |
| Additional Sensor Information 1164 |
| Additional Information about Data 1166 |
| ... |

FIGURE 11

LONG-TERM DATA STORAGE SERVICE FOR WEARABLE DEVICE DATA

BACKGROUND

Unless otherwise indicated herein, the materials described in this section are not prior art to the claims in this application and are not admitted to be prior art by inclusion in this section.

Computing systems such as personal computers, laptop computers, tablet computers, cellular phones, and countless types of Internet-capable devices are prevalent in numerous aspects of modern life. Over time, the manner in which these devices are providing information to users is becoming more intelligent, more efficient, more intuitive, and/or less obtrusive.

The trend toward miniaturization of computing hardware, peripherals, as well as of sensors, detectors, and image and audio processors, among other technologies, has helped open up a field sometimes referred to as "wearable computing." For example, some wearable computing devices are wrist-mounted devices that can be worn like a wrist watch.

Many wearable computing devices can store and communicate data about the wearable computing device, other objects, and/or other entities, such as a wearer of the wearable computing device. Once communicated, data from the wearable computing device can in turn be stored on one or more other computing devices.

SUMMARY

In one aspect, a method is provided. A computing device receives a plurality of data items about a biological entity from a plurality of sources. The plurality of sources includes a wearable device being worn by the biological entity and the plurality of data items includes a data item that includes physiological data obtained by one or more sensors of the wearable device. The computing device verifies each data item of the plurality of data items by at least: determining a source of the data item from among the plurality of sources, determining a provenance for the data item associated with the source of the data item, and verifying that the data item is associated with the biological entity based at least on the a provenance for the data item associated with the source of the data item. After verifying that a particular data item is associated with the biological entity, the computing device stores the particular data item in a data log associated with the biological entity.

In another aspect, a computing device is provided. The wearable computing device includes a processor and a non-transitory computer readable medium. The non-transitory computer readable medium is configured to store at least a data log associated with a biological entity and executable instructions. The executable instructions, when executed by the processor, cause the computing device to perform functions including: receiving a plurality of data items about the biological entity from a plurality of sources, the plurality of sources including a wearable device being worn by the biological entity and the plurality of data items including a data item that includes physiological data obtained by one or more sensors of the wearable device; verifying each data item of the plurality of data items by at least: determining a source of the data item from among the plurality of sources, determining a provenance for the data item associated with the source of the data item, and verifying that the data item is associated with the biological entity based at least on the provenance for the data item associated with the source of the data item; and after verifying that a particular data item is associated with the biological entity, storing the particular data item in the data log associated with the biological entity.

In another aspect, a non-transitory computer readable medium is provided. The non-transitory computer readable medium is configured to store at least executable instructions. The executable instructions, when executed by a processor of a computing device, cause the computing device to perform functions including: receiving a plurality of data items about a biological entity from a plurality of sources, the plurality of sources including a wearable device being worn by the biological entity and the plurality of data items including a data item that includes physiological data obtained by one or more sensors of the wearable device; verifying each data item of the plurality of data items by at least: determining a source of the data item from among the plurality of sources, determining a provenance for the data item associated with the source of the data item, and verifying that the data item is associated with the biological entity based at least on the provenance for the data item associated with the source of the data item; and after verifying that a particular data item is associated with the biological entity, storing the particular data item in a data log associated with the biological entity.

In another aspect, a wearable computing device is provided. The wearable computing device comprises: means for storing a data log associated with a biological entity; means for receiving a plurality of data items about the biological entity from a plurality of sources, the plurality of sources including a wearable device being worn by the biological entity and the plurality of data items including a data item that includes physiological data obtained by one or more sensors of the wearable device; means for verifying each data item of the plurality of data items comprising: means for determining a source of the data item from among the plurality of sources, means for determining a provenance for the data item associated with the source of the data item, and means for verifying that the data item is associated with the biological entity based at least on the provenance for the data item associated with the source of the data item; and means for, after verifying that a particular data item is associated with the biological entity, storing the particular data item in the means for storing the data log associated with the biological entity.

BRIEF DESCRIPTION OF THE DRAWINGS

FIG. 11 depicts an example data format, in accordance with an example embodiment.

DETAILED DESCRIPTION

Figure 1:
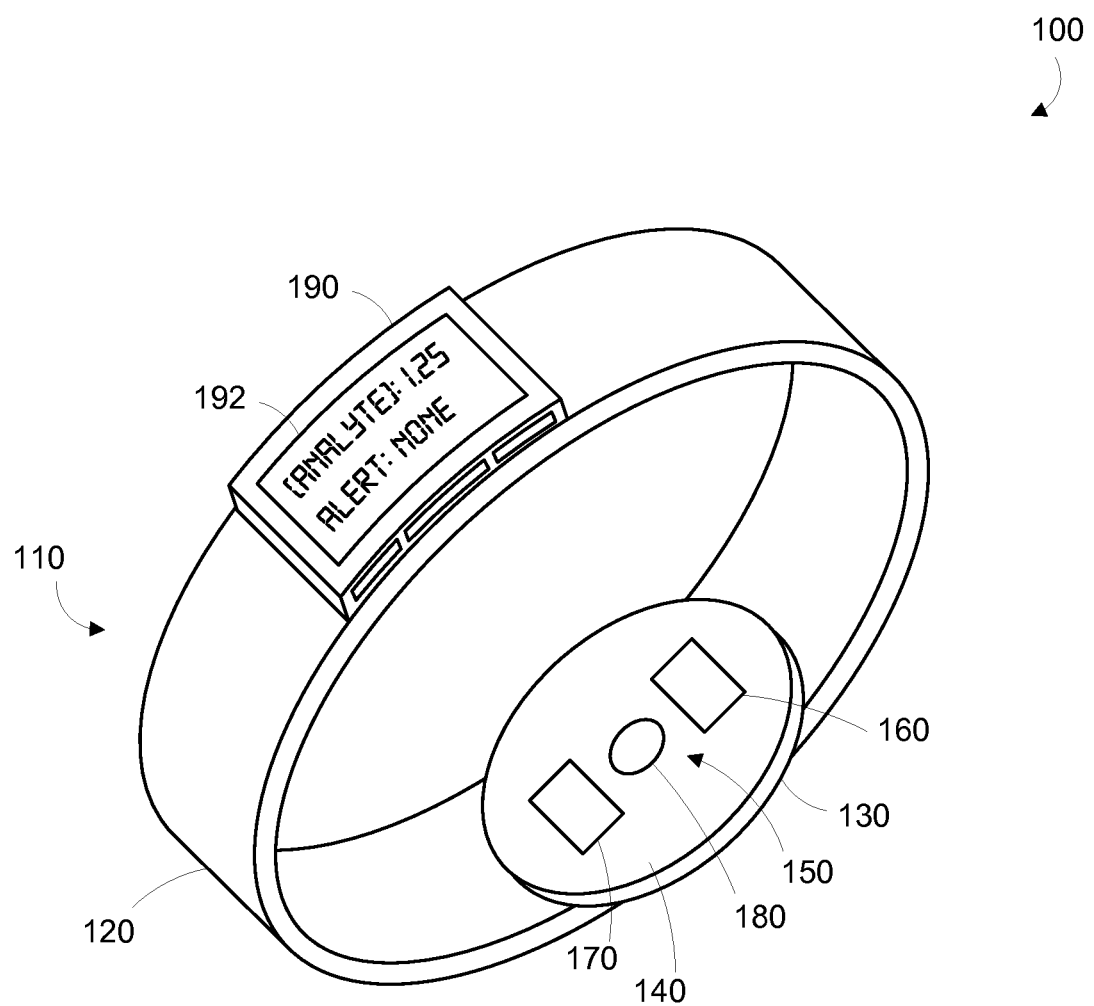
FIG. 1 is a perspective view of an example wearable device, in accordance with an example embodiment.

Long-Term Data Storage Service for Wearable Device Data

An example wearable device is a wearable computing device that automatically detects, measures, and possibly stores data about a wearer wearing a device, where the data can include physiological and environmental parameters. The physiological parameters could include any parameters that may relate to the health of the wearer and the environmental parameters may relate to an environment about the wearer. To measure the physiological parameters, the wearable device can include sensors for measuring blood pressure, pulse rate, skin temperature, and/or one or more analytes in blood circulating in subsurface vasculature proximate to the wearable device. For example, the one or more analytes can include enzymes, hormones, proteins, cells or other molecules. In some cases, the wearable device can include sensors to measure environmental parameters related to the wearer, such as location, temperature, humidity, wind speed/direction, time of day, and illumination parameters.

The wearable device can include a mount that is configured to mount the device to a specific surface of the person's body, more particularly, to a body location where subsurface vasculature is readily observable. For example, the wearable device can include a wristband for mounting the wearable device on the wrist. In this position, the wearable device may be only about 2-4 millimeters away from the midpoint of an artery, capillary or vein in the wrist. In other cases, the wearable device can be mounted on/near other body locations.

The wearable device can further include memory for storing data, such as but not limited to the physiological parameters and/or results of the data analysis, and a communication interface for transmitting at least stored data to medical personnel and/or receiving instructions or recommendations based on those results. In some examples, the communication interface is a wireless communication interface. The communication interface may also include a universal serial bus (USB) interface, a secure digital (SD) card interface, a wired interface, or any other appropriate interface for communicating data from the device to a server. The term "server" may include any system or device that responds to requests across a computer network to provide, or helps to provide, a network service, and may include servers run on dedicated computers, mobile devices, and those operated in a cloud computing network.

Data can be communicated from the wearable device to other devices, such as associated computing devices and servers. Example associated computing devices include but are not limited to, smart phones, laptop computers, desktop computers, and tablet computers. The associated computing devices can provide functionality that may be difficult or impossible for the wearable devices, such as providing additional computing power, storage, communications interfaces, and/or user interfaces.

For example, one or more other devices can provide long-term storage for the data communicated from the wearable device. The data can include, but is not limited to, data associated with a biological entity. Example biological entities include, but are not limited to, living human beings, deceased human beings, other living organisms, and other deceased organisms. The data associated with the biological entity can include:

Physiological data, such as, but not limited to, physiological data obtained via sensors of a wearable device while the wearable device is worn by the biological entity.

Environmental data, such as, but not limited to, data provided by a computing device associated with the biological entity; e.g., temperature data, location data, velocity data, etc. Example computing devices include, but are not limited to, a smart phone, a laptop computer, a desktop computer, and a tablet device.

Demographic data, such as age, gender, occupation, employer, residence information, etc. that is applicable to the biological entity.

Medical data associated with the biological entity, such as but not limited to, medical records for the biological entity, epidemiological data related to the biological entity, genetic information related to the biological entity, medical data about a family of the biological entity, disease records, vaccination records, and information about pharmaceuticals and/or other substances consumed by the biological entity.

Other sources of data about the biological entity; e.g., news sources, and sources of information from associates (friends, family, co-workers, etc.) of the biological entity.

Self-reported data on activities, mood, physical status, emotional status, mental state, health-related and other goals, dietary information, etc. that can be provided using the wearable device and/or from other sources. For example, the wearable device can have a diary or annotation function so that the biological entity wearing the wearable device can provide self-reported data;

e.g., "I just started my workout", "I shouldn't have eaten all those tomatoes", perhaps using a voice interface, a text interface, or some other user interface. Other sources can include, but are not limited to, computing device(s) associated with the biological entity, social-networking and/or other accounts associated with the biological entity.

Other than perhaps the self-reported data, the data associated with the biological entity can be obtained passively; that is, without the intervention of the biological entity or other entity. Rather, the data listed above can be obtained by (a) receiving consent by the biological entity to obtain and store the data and (b) wearing a wearable device and perhaps use/carry an associated computing device to obtain the above-mentioned physiological and environmental data. The demographic data, medical data, and other sources of data can be obtained and stored without the intervention of the biological entity as long as the obtained data is data obtained by the consent of the biological entity. In some cases, another biological entity can provide the necessary consent; e.g., a parent of a minor child, an owner of a pet with a wearable device, etc.

The data can be stored by one or more biological-entity data storage (BEDS) devices, such as one or more networked computer server and/or storage devices, for at least the lifespan of the biological entity; e.g., for a period of years, decades, and, in some scenarios, even longer. As indicated above, stored data can come from a variety of sources. In some cases, those sources may or may not be associated with the biological entity. Then, before data is stored, the data and/or data sources can be verified before storage. One technique for verifying data and/or a data source involves determining a provenance of the data and/or data source. A provenance for an item can includes metadata about the item, including but not limited to, information about the timing, custody, and/or location about the item. Example information in a provenance for data and/or a data source D can include information about location(s), time(s), network address(es) (e.g., IP address(es), MAC address(es), domain names including FQDNs), and geographical location(s) associated with D.

Once data and/or a data source have been verified, data can be stored in long term storage of the BEDS devices. The data can be stored using a standard storage format. For example, the data can be stored in a standardly-formatted data record that includes: an identifier and/or other information about the biological entity, timing information, a type, and the data itself. The type can be a type of data (e.g., blood-pressure, biological temperature, atmospheric temperature, self-reported mood), a type of activity associated with the data (e.g., working out, sleeping, eating), a type of data source (e.g., a sensor identifier, a wearable-device identifier, device manufacturer/model/year of manufacture etc.), other types, and combinations thereof. By using a standard storage format, data from a wide variety of sources and devices can be stored by BEDS devices over time. For example, over a lifespan of the biological entity, the biological entity can use several wearable devices to provide physiological and perhaps other data. Data received at a BEDS device can be converted as needed to a data record using the standard storage format and then stored in a data record associated with the biological entity.

After data is stored, the BEDS devices can be queried by authorized entities to obtain data about the biological entity. For example, queries to the BEDS device can request data about glucose levels over time for the biological entity to explore trends in the requested data about diabetes or other diseases related to glucose levels. An entity can be authorized to receive data based on the role of the entity; e.g., physiological data can be obtained by entities having medically-related roles and authorized by the biological entity, while demographic data can be obtainable by a sociologist authorized by the biological entity. In some cases, authorized entities can further delegate access to data stored in a BEDS device; e.g., a parent can authorize medical personnel to obtain physiological data about the parent's child from the BEDS device.

By obtaining and storing a large amount of data about a biological entity for long time-spans, particularly physiological data, a significantly larger amount of medical information can be made available to help diagnose and/or treat medical conditions of the biological entity. For example, this long-term, large-scale data storage can lead to more accurate diagnoses of medical conditions and can lead to possible preventative measures to avoid or mitigate medical conditions.

Example Wearable Devices

A wearable device 100 can automatically measure a plurality of physiological parameters of a person wearing the device. The term "wearable device," as used in this disclosure, refers to any device that is capable of being worn at, on or in proximity to a body surface, such as a wrist, ankle, waist, chest, or other body part. In order to take in vivo measurements in a non-invasive manner from outside of the body, the wearable device may be positioned on a portion of the body where subsurface vasculature is easily observable, the qualification of which will depend on the type of detection system used. The device may be placed in close proximity to the skin or tissue, but need not be touching or in intimate contact therewith. A mount 110, such as a belt, wristband, ankle band, etc. can be provided to mount the device at, on or in proximity to the body surface. The mount 110 may prevent the wearable device from moving relative to the body to reduce measurement error and noise. In one example, shown in FIG. 1, the mount 110, may take the form of a strap or band 120 that can be worn around a part of the body. Further, the mount 110 may be an adhesive substrate for adhering the wearable device 100 to the body of a wearer.

A measurement platform 130 is disposed on the mount 110 such that it can be positioned on the body where subsurface vasculature is easily observable. An inner face 140 of the measurement platform is intended to be mounted facing to the body surface. The measurement platform 130 may house the data collection system 150, which may include at least one detector 160 for detecting at least one physiological parameter, which could include any parameters that may relate to the health of the person wearing the wearable device. For example, the detector 160 could be configured to measure blood pressure, pulse rate, respiration rate, skin temperature, etc. At least one of the detectors 160 is configured to non-invasively measure one or more analytes in blood circulating in subsurface vasculature proximate to the wearable device. In a non-exhaustive list, detector 160 may include any one of an optical (e.g., CMOS, CCD, photodiode), acoustic (e.g., piezoelectric, piezoceramic), electrochemical (voltage, impedance), thermal, mechanical (e.g., pressure, strain), magnetic, or electromagnetic (e.g., magnetic resonance) sensor. The components of the data collection system 150 may be miniaturized so that the wearable device may be worn on the body without significantly interfering with the wearer's usual activities.

In an example embodiment, the wearable device obtains at least some of the health-related information by detecting the binding of a clinically-relevant analyte to functionalized particles, for example, microparticles or nanoparticles introduced into a lumen of the subsurface vasculature. The term "binding" is understood in its broadest sense to also include a detectable interaction between the clinically relevant analyte and the functionalized particles. The particles can have a diameter that is less than about 20 micrometers. In some embodiments, the particles have a diameter on the order of about 10 nm to 1 μm. In further embodiments, small particles on the order of 10-100 nm in diameter may be assembled to form a larger "clusters" or "assemblies" on the order of 1-10 micrometers. Those of skill in the art will understand a "particle" in its broadest sense and that it may take the form of any fabricated material, a molecule, cryptophane, a virus, a phage, etc. Further, a particle may be of any shape, for example, spheres, rods, non-symmetrical shapes, etc.

In some examples, the particles may be magnetic and can be formed from a paramagnetic, super-paramagnetic or ferromagnetic material or any other material that responds to a magnetic field. Alternatively, the particles may also be made of non-magnetic materials such as polystyrene.

The particles, or a group of several particles in a complex, may be functionalized with a receptor that has a specific affinity to bind to or interact with a clinically relevant analyte. The receptor may be inherent to the particle itself. For example, the particle itself may be a virus or a phage with an inherent affinity for certain analytes. Additionally or alternatively, the particles can be functionalized by covalently attaching a receptor that specifically binds or otherwise recognizes a particular clinically-relevant analyte. The functionalized receptor can be an antibody, peptide, nucleic acid, phage, bacteria, virus, or any other molecule with a defined affinity for a target analyte. Other compounds or molecules, such as fluorophores or autofluorescent or luminescent markers, which may assist in interrogating the particles in vivo, may also be attached to the particles.

The functionalized particles can be introduced into the person's blood stream by injection, ingestion, inhalation, transdermally, or in some other manner. Where magnetic particles are used, the wearable device may include a magnet that can direct into the portion of subsurface vasculature a magnetic field that is sufficient to cause the functionalized magnetic particles to collect in a lumen of that portion of subsurface vasculature. However, measurements may be taken without localized "collection" of the functionalized particles. The wearable device may be configured to activate the magnetic periodically, such as at certain times of every day (e.g., every hour).

In some examples, the data collection system 150 further includes a signal source 170 for transmitting an interrogating signal that can penetrate the wearer's skin into the portion of subsurface vasculature, for example, into a lumen of the subsurface vasculature. The interrogating signal can be any kind of signal that is benign to the wearer, such as electromagnetic, magnetic, optic, acoustic, thermal, mechanical, and results in a response signal that can be used to measure a physiological parameter or, more particularly, that can detect the binding of the clinically-relevant analyte to the functionalized particles. In one example, the interrogating signal is an electromagnetic pulse (e.g., a radio frequency (RF) pulse) and the response signal is a magnetic resonance signal, such as nuclear magnetic resonance (NMR). In another example, the interrogating signal is a time-varying magnetic field, and the response signal is an externally-detectable physical motion due to the time-varying magnetic field. The time-varying magnetic field modulates the particles by physical motion in a manner different from the background, making them easier to detect. In a further example, the interrogating signal is an electromagnetic radiation signal. In particular, the interrogating signal may be electromagnetic radiation having a wavelength between about 400 nanometers and about 1600 nanometers. The interrogating signal may, more particularly, comprise electromagnetic radiation having a wavelength between about 500 nanometers and about 1000 nanometers. In some examples, the functionalized particles include a fluorophore. The interrogating signal may therefore be an electromagnetic radiation signal with a wavelength that can excite the fluorophore and penetrate the skin or other tissue and subsurface vasculature (e.g., a wavelength in the range of about 500 to about 1000 nanometers), and the response signal is fluorescence radiation from the fluorophore that can penetrate the subsurface vasculature and tissue to reach the detector.

In some cases, an interrogating signal is not necessary to measure one or more of the physiological parameters and, therefore, the wearable device 100 may not include a signal source 170. For example, the functionalized particles include an autofluorescent or luminescent marker, such as a fluorophore, that will automatically emit a response signal indicative of the binding of the clinically-relevant analyte to the functionalized particles, without the need for an interrogating signal or other external stimulus. In some examples, the functionalized particles may include a chemoluminescent marker configured to produce a response signal in the form of fluorescence radiation produced in response to a chemical reaction initiated, at least in part, to the binding of the target analyte to the particle.

A collection magnet 180 may also be included in the data collection system 150. In such embodiments, the functionalized particles may also be made of or be functionalized with magnetic materials, such as ferromagnetic, paramagnetic, super-paramagnetic, or any other material that responds to a magnetic field. The collection magnet 180 is configured to direct a magnetic field into the portion of subsurface vasculature that is sufficient to cause functionalized magnetic particles to collect in a lumen of that portion of subsurface vasculature. The magnet may be an electromagnet that may be turned on during measurement periods and turned off when a measurement period is complete so as to allow the magnetic particles to disperse through the vasculature.

The wearable device 100 may also include a user interface 190 via which the wearer of the device may receive one or more recommendations or alerts generated either from a remote server or other remote computing device, or from a processor within the device. The alerts could be any indication that can be noticed by the person wearing the wearable device. For example, the alert could include a visual component (e.g., textual or graphical information on a display), an auditory component (e.g., an alarm sound), and/or tactile component (e.g., a vibration). Further, the user interface 190 may include a display 192 where a visual indication of the alert or recommendation may be displayed. The display 192 may further be configured to provide an indication of the measured physiological parameters, for instance, the concentrations of certain blood analytes being measured.

Figure 2A:
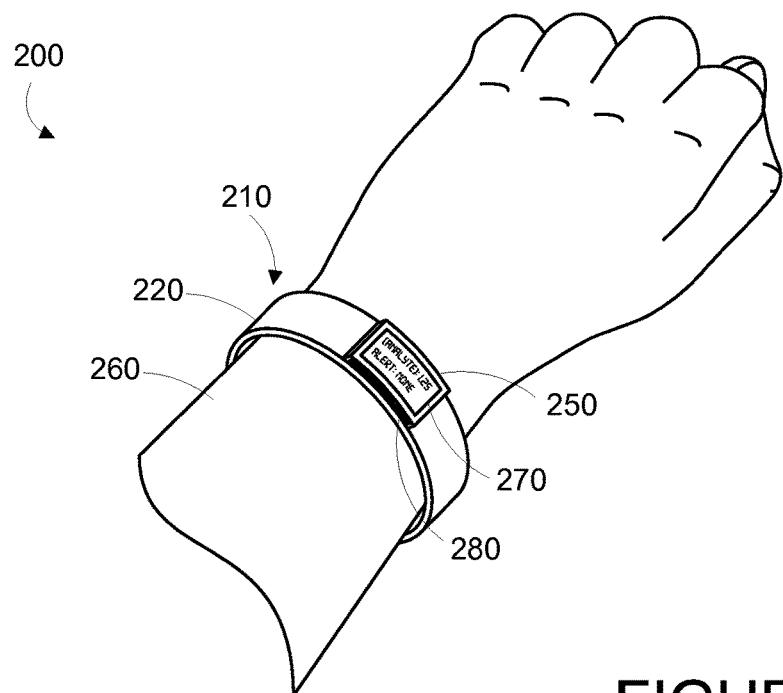
FIG. 2A is a perspective top view of an example wrist-mounted device, when mounted on a wearer's wrist, in accordance with an example embodiment.
Figure 2B:
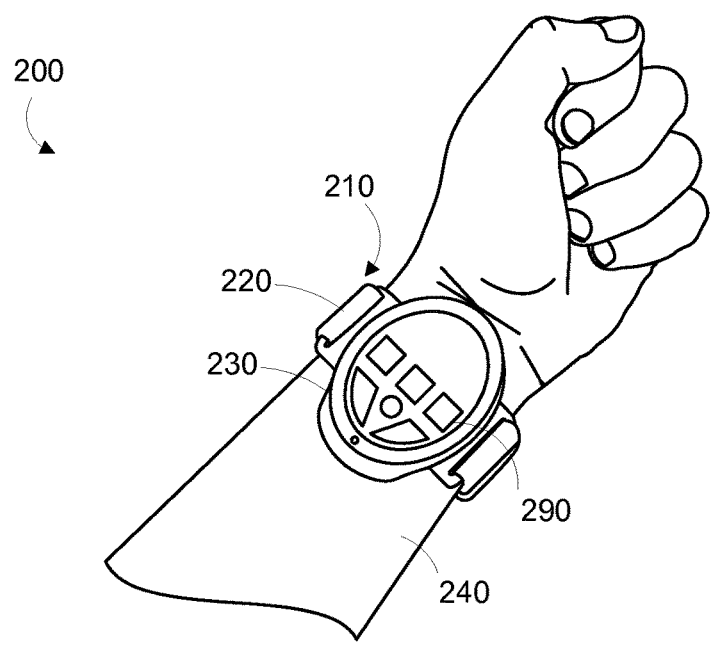
FIG. 2B is a perspective bottom view of an example wrist-mounted device shown in FIG. 2A, when mounted on a wearer's wrist, in accordance with an example embodiment.

In one example, the wearable device is provided as a wrist-mounted device, as shown in FIGS. 2A, 2B, 3A-3C, 4A, 4B, 5, and 6. The wrist-mounted device may be mounted to the wrist of a living subject with a wristband or cuff, similar to a watch or bracelet. As shown in FIGS. 2A and 2B, the wrist mounted device 200 may include a mount 210 in the form of a wristband 220, a measurement platform 230 positioned on the anterior side 240 of the wearer's wrist, and a user interface 250 positioned on the posterior side 260 of the wearer's wrist. The wearer of the device may receive, via the user interface 250, one or more recommendations or alerts generated either from a remote server or other remote computing device, or alerts from the measurement platform. Such a configuration may be perceived as natural for the wearer of the device in that it is common for the posterior side 260 of the wrist to be observed, such as the act of checking a wrist-watch. Accordingly, the wearer may easily view a display 270 on the user interface. Further, the measurement platform 230 may be located on the anterior side 240 of the wearer's wrist where the subsurface vasculature may be readily observable. However, other configurations are contemplated.

The display 270 may be configured to display a visual indication of the alert or recommendation and/or an indication of the measured physiological parameters, for instance, the concentrations of certain blood analytes being measured. Further, the user interface 250 may include one or more buttons 280 for accepting inputs from the wearer. For example, the buttons 280 may be configured to change the text or other information visible on the display 270. As shown in FIG. 2B, measurement platform 230 may also include one or more buttons 290 for accepting inputs from the wearer. The buttons 290 may be configured to accept inputs for controlling aspects of the data collection system, such as initiating a measurement period, or inputs indicating the wearer's current health state (i.e., normal, migraine, shortness of breath, heart attack, fever, "flu-like" symptoms, food poisoning, etc.).

Figure 3A:
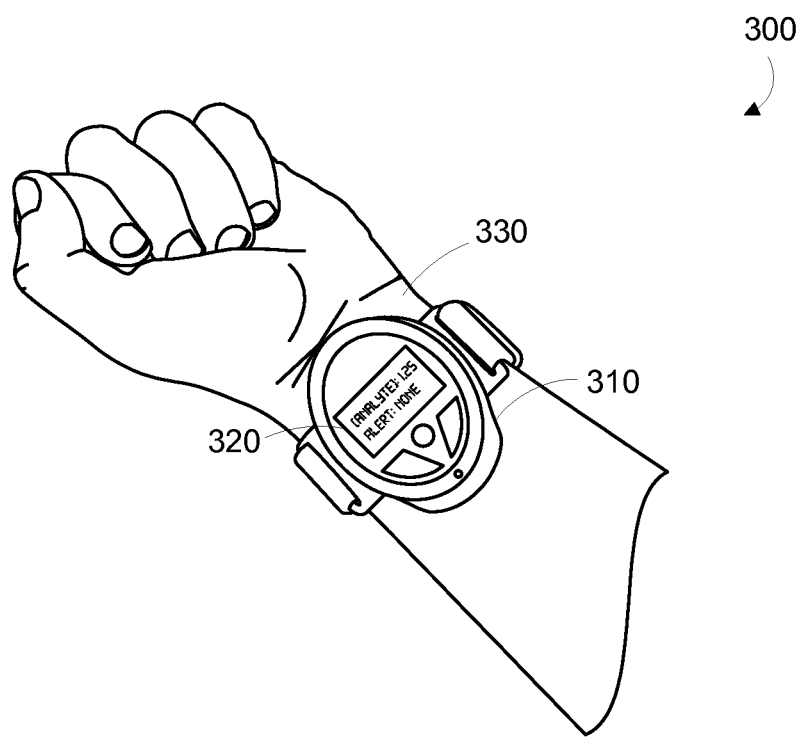
FIG. 3A is a perspective bottom view of an example wrist-mounted device, when mounted on a wearer's wrist, in accordance with an example embodiment.
Figure 3B:
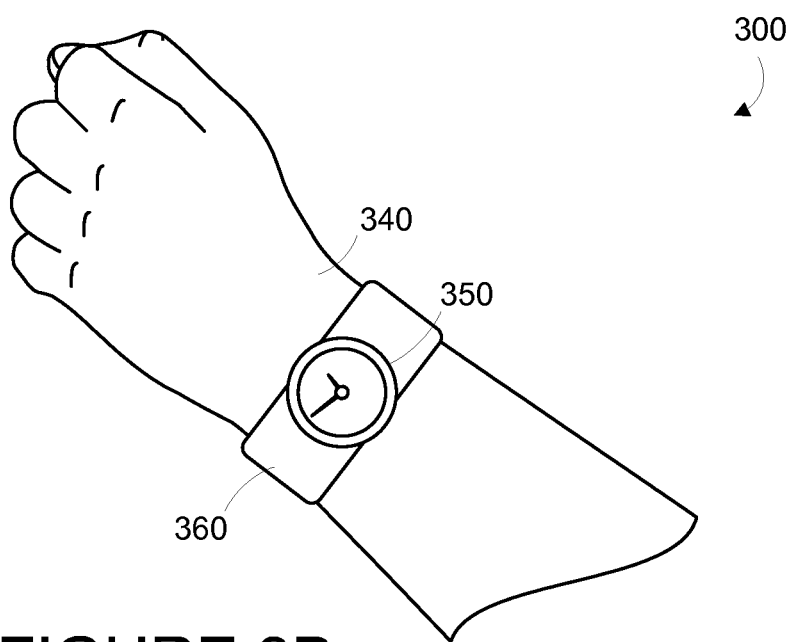
FIG. 3B is a perspective top view of an example wrist-mounted device shown in FIG. 3A, when mounted on a wearer's wrist, in accordance with an example embodiment.
Figure 3C:
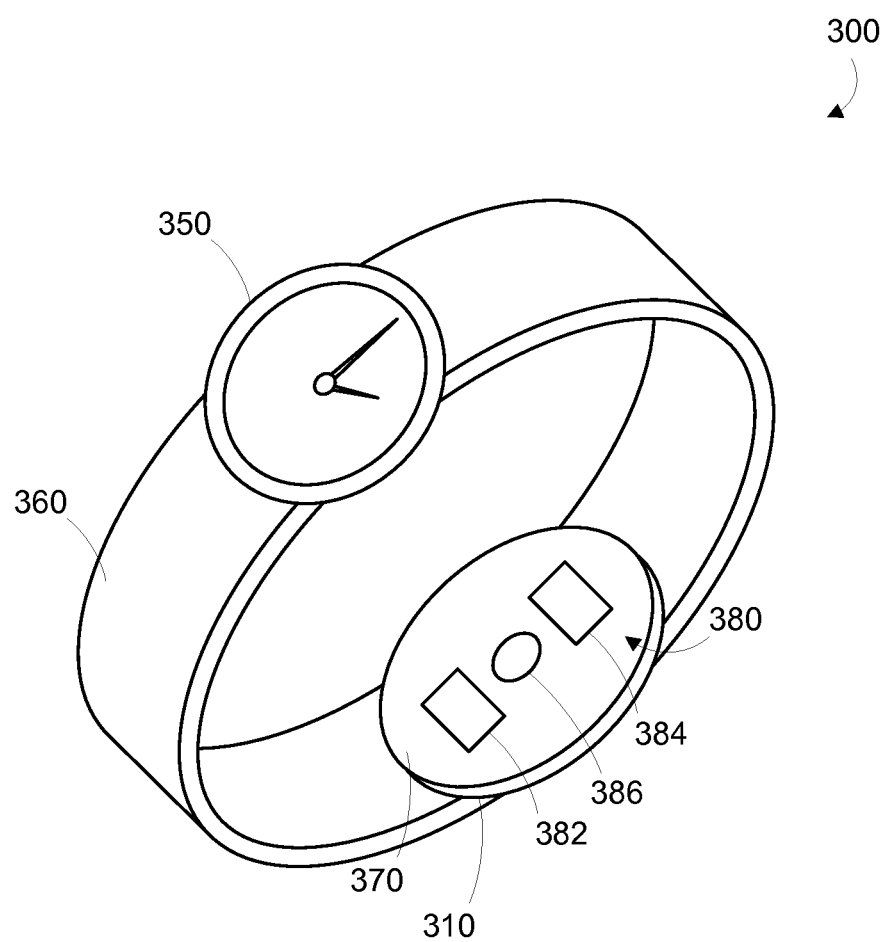
FIG. 3C is a perspective view of an example wrist-mounted device shown in FIGS. 3A and 3B, in accordance with an example embodiment.

In another example wrist-mounted device 300, shown in FIGS. 3A-3C, the measurement platform 310 and user interface 320 are both provided on the same side of the wearer's wrist, in particular, the anterior side 330 of the wrist. On the posterior side 340, a watch face 350 may be disposed on the strap 360. While an analog watch is depicted in FIG. 3B, one of skill in the art will recognize that any type of clock may be provided, such as a digital clock.

As can be seen in FIG. 3C, the inner face 370 of the measurement platform 310 is intended to be worn proximate to the wearer's body. A data collection system 380 housed on the measurement platform 310 may include a detector 382, a signal source 384 and a collection magnet 386. As described above, the signal source 384 and the collection magnet 386 may not be provided in all embodiments of the wearable device.

Figure 4A:
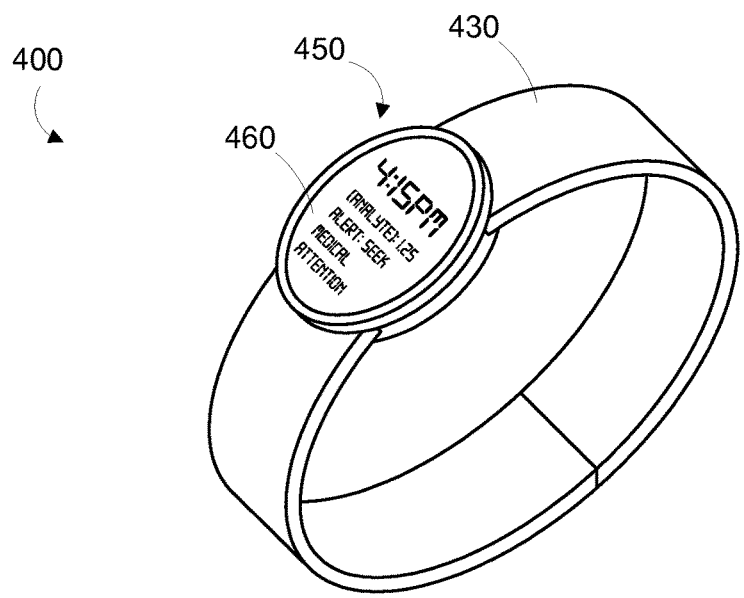
FIG. 4A is a perspective view of an example wrist-mounted device, in accordance with an example embodiment.
Figure 4B:
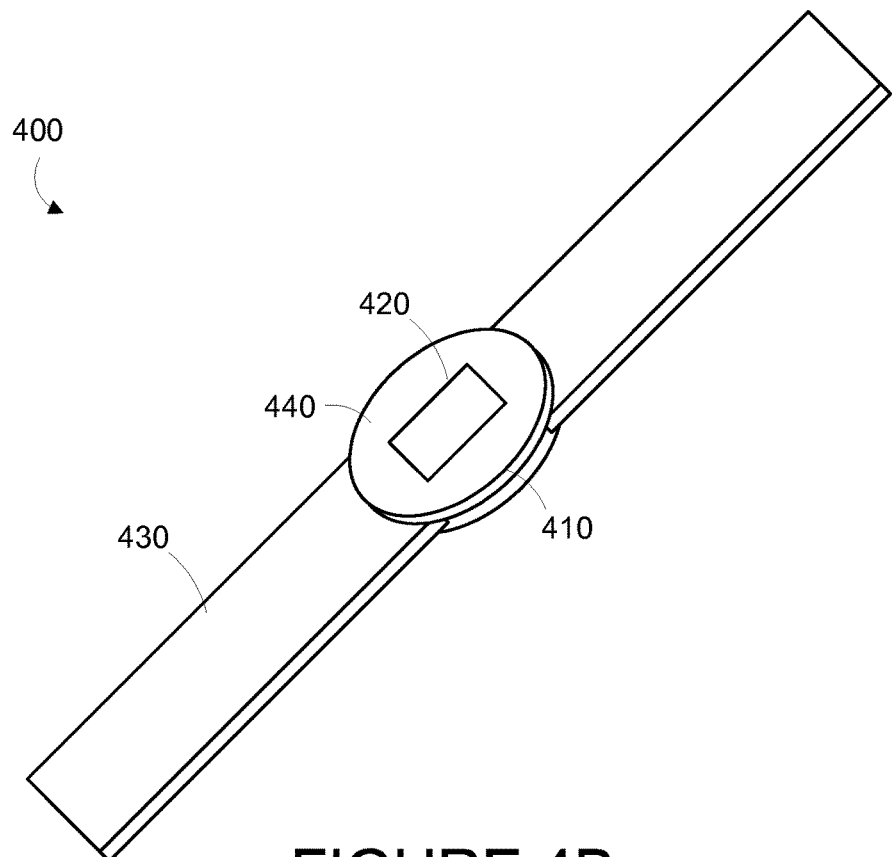
FIG. 4B is a perspective bottom view of an example wrist-mounted device shown in FIG. 4A, in accordance with an example embodiment.

In a further example shown in FIGS. 4A and 4B, a wrist mounted device 400 includes a measurement platform 410, which includes a data collection system 420, disposed on a strap 430. Inner face 440 of measurement platform may be positioned proximate to a body surface so that data collection system 420 may interrogate the subsurface vasculature of the wearer's wrist. A user interface 450 with a display 460 may be positioned facing outward from the measurement platform 410. As described above in connection with other embodiments, user interface 450 may be configured to display data collected from the data collection system 420, including the concentration of one or more measured analytes, and one or more alerts generated by a remote server or other remote computing device, or a processor located on the measurement platform. The user interface 420 may also be configured to display the time of day, date, or other information that may be relevant to the wearer.

Figure 5:
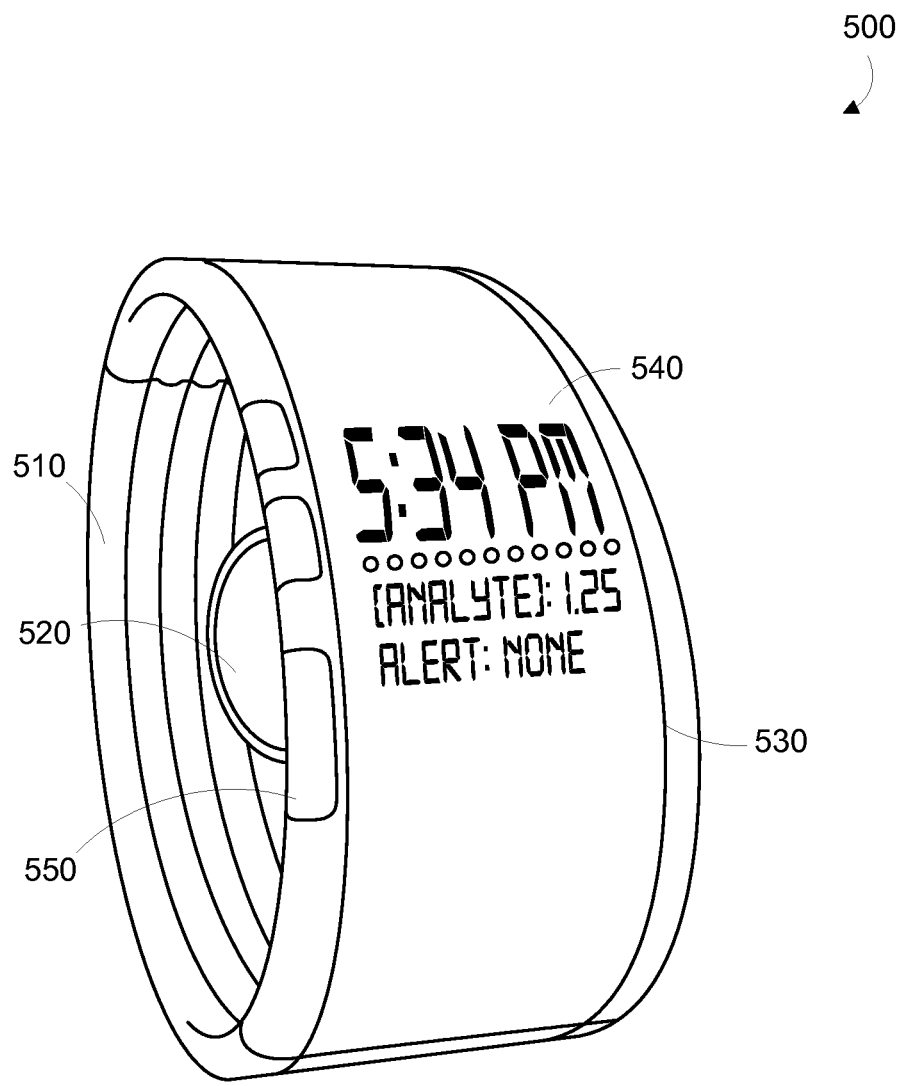
FIG. 5 is a perspective view of an example wrist-mounted device, in accordance with an example embodiment.
Figure 6:
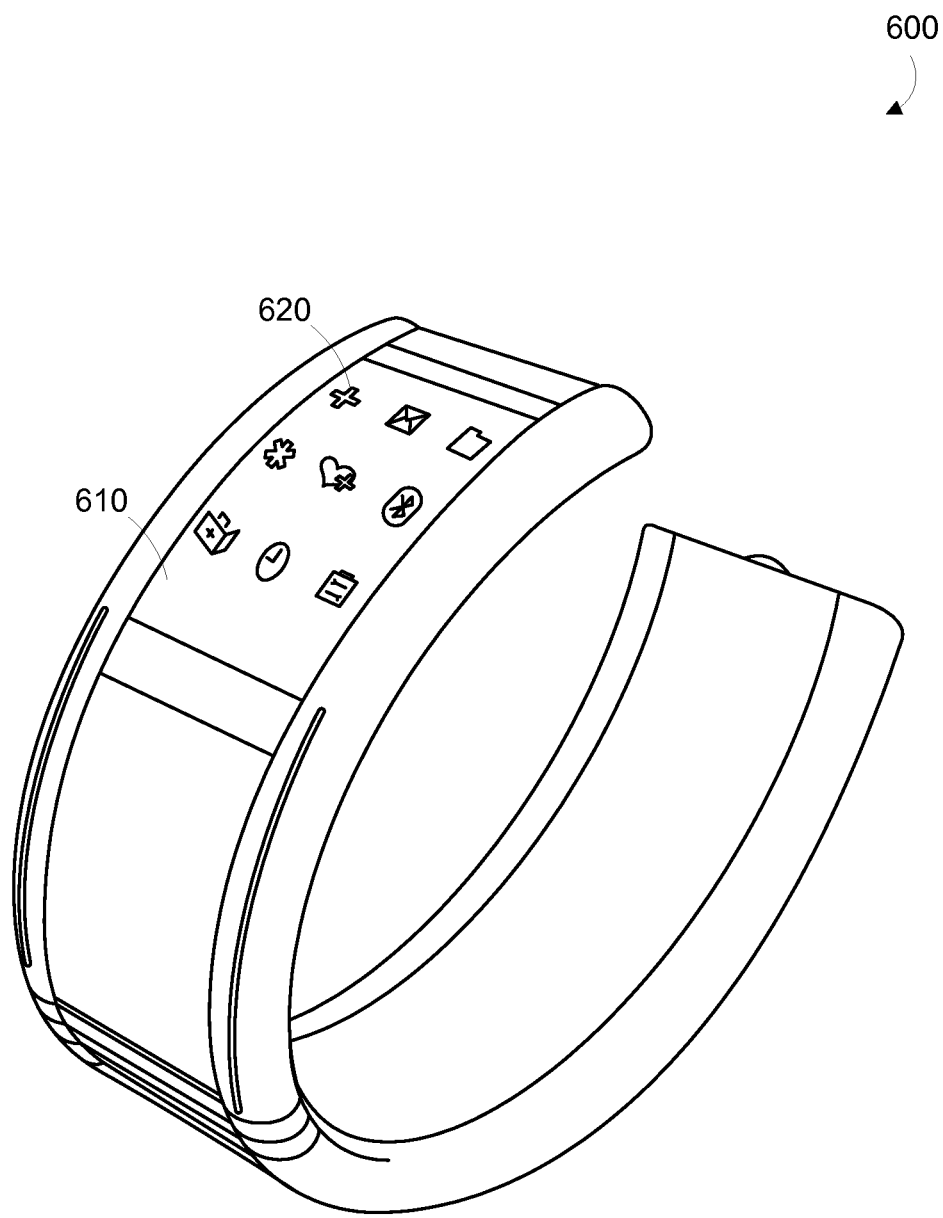
FIG. 6 is a perspective view of an example wrist-mounted device, in accordance with an example embodiment.

As shown in FIG. 5, in a further embodiment, wrist-mounted device 500 may be provided on a cuff 510. Similar to the previously discussed embodiments, device 500 includes a measurement platform 520 and a user interface 530, which may include a display 540 and one or more buttons 550. The display 540 may further be a touch-screen display configured to accept one or more input by the wearer. For example, as shown in FIG. 6, display 610 may be a touch-screen configured to display one or more virtual buttons 620 for accepting one or more inputs for controlling certain functions or aspects of the wearable device 600, or inputs of information by the user, such as current health state.

Figure 7:
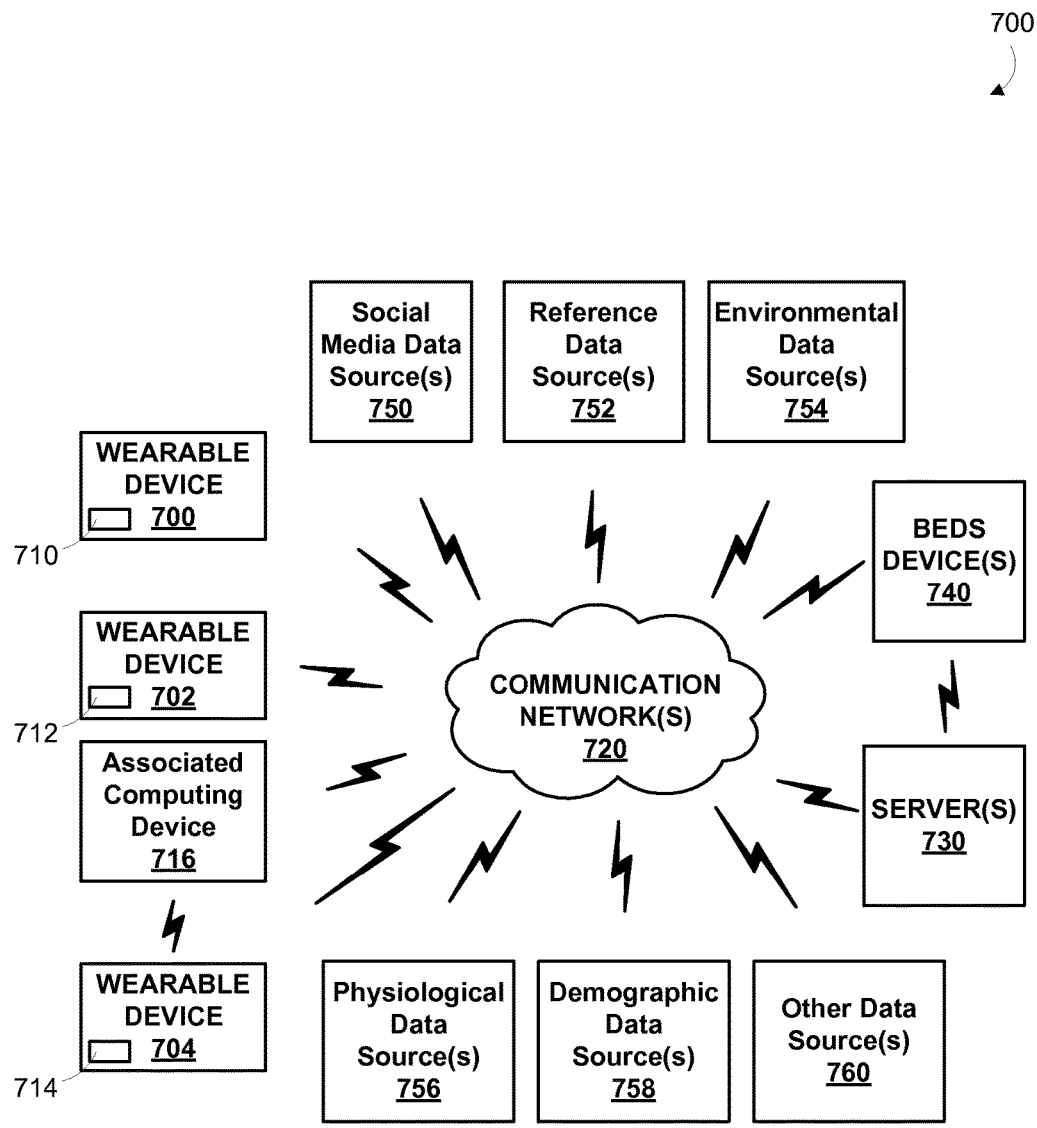
FIG. 7 is a block diagram of an example system that includes a plurality of wearable devices and a plurality of data sources in communication with server(s) and biological-entity data storage (BEDS) device(s), in accordance with an example embodiment.

FIG. 7 is a block diagram of system 700 that includes a plurality of wearable devices 700, 702, 704 and a plurality of data sources 750, 752, 754, 756, 758, 760 in communication with server(s) 730 and BEDS device(s) 740. Wearable devices 700, 702, 704 can be configured to transmit data via respective communication interfaces 710, 712, 714 over one or more communication networks 720 to a remote server 730. In some embodiments, one or more of communication interfaces 710, 712, 714 can include a wireless transceiver for sending and receiving communications to and from the server 730. In further embodiments, one or more of communication interfaces 710, 712, 714 can include wired and wireless communication interfaces for the transfer of data. For example, one or more of communication interfaces 710, 712, 714 can include a universal serial bus (USB) interface or a secure digital (SD) card interface.

Communication networks 720 can be any one of: a plain old telephone service (POTS) network, a cellular network, a wired network, a fiber network, a wireless network and a data network. Server(s) 730 may include any type of remote computing device or remote cloud computing network. Further, communication network 720 can include one or more intermediaries; for example, wearable device 704 can transmit data to associated computing device 716 that in turn can transmit the data from wearable device 704 to server(s) 730. Examples of associated computing device 716 include, but are not limited to, a mobile phone, smart phone, or other personal computing device. In some scenarios as indicated in FIG. 7, wearable device 704 can transmit to communication network 720 directly as well.

In addition to receiving communications from wearable devices 700, 702, 704, such as collected physiological parameter data and data regarding health state as input by respective wearers of wearable devices 700, 702, 704, server(s) 730 can also be configured to gather and/or receive either from the wearable device 700 or from one or more other data sources, information regarding a wearer, the wearer's overall medical history, environmental factors and geographical data. Examples of these other data sources include social media data source(s) 750 for social media data associated with the wearer, reference data source(s) 754 for reference data associated with physiological and/or other types of data associated with the wearer and/or wearable device, environmental data source(s) 756 for data associated with an environment for the wearer (e.g., health-related environmental data from the Centers for Disease Control (CDC), National Health Service, and similar sources; weather, pollution and allergen data from the National Weather Service and similar sources; traffic, news, and/or other information about the environment for the wearer), demographic data source(s) 758 for demographic and other population-associated data associated with a wearer and/or wearable device, and other data source(s) 760.

Data about a wearer (or other entity) can be stored on BEDS device(s) 740. For example, a user account may be established on server(s) 730 for a wearer, where the account contains information about the wearer's medical history, and where some or all of the information about the wearer's medical history is stored on BEDS device(s) 740. Moreover, in some examples, the server 730 may be configured to regularly receive information from some or all of data sources 750-760. Then, some or all of the received information from data sources 750-760 can be stored with the wearer's account; e.g., on BEDS device(s) 740. Further, server(s) 730 and/or BEDS device(s) 740 can be configured to communicate and store data regarding a wearer's health state from a hospital or physician. Such information may be used in the server's decision-making process, such as recognizing correlations and in generating clinical protocols.

Data associated with the wearer received (and later stored) at server(s) 730 and/or BEDS device(s) 740 can include provenance data. Provenance data can include data about the received and/or stored data, such as, but not limited to, information about a time of data reception, a type of data, and/or an address of the device providing the data. In some embodiments, provenance data can include a geographical location of the device. Such location information can be used to detect and monitor spatial and temporal spreading of diseases. As such, wearable device 700, 702, 704 can be configured to determine and/or provide an indication of its own location. Wearable device 700, 702, 704 can be configured to provide location information by itself and/or in conjunction with an associated computing device; e.g., associated computing device 716. For example, a wearable device and/or an associated computing device may include a GPS system so that it can include GPS location information (e.g., GPS coordinates) in a communication to server(s) 730 and/or BEDS device(s) 740. As another example, a wearable device may use a technique that involves triangulation (e.g., between base stations in a cellular network) to determine its location. Other location-determination techniques are also possible.

Server(s) 730 may also be configured to make determinations regarding the efficacy of a drug or other treatment based on information regarding the drugs or other treatments received by a wearer of the device and, at least in part, the physiological parameter data and the indicated health state of the user derived from data stored on BEDS device(s) 740. From this information, server(s) 730 can be configured to derive an indication of the effectiveness of the drug or treatment. For example, if a drug is intended to treat nausea and the wearer of the device does not indicate that he or she is experiencing nausea after beginning a course of treatment with the drug, the server may be configured to derive an indication that the drug is effective for that wearer. In another example, a wearable device may be configured to measure blood glucose. If a wearer is prescribed a drug intended to treat diabetes, but the server receives data from the wearable device indicating that the wearer's blood glucose has been increasing over a certain number of measurement periods, the server may be configured to derive an indication that the drug is not effective for its intended purpose for this wearer.

Further, some embodiments of the system may include privacy controls which may be automatically implemented or controlled by the wearer of the device. As one example, discussed below in the context of FIG. 10, the wearer (or other entity) can control data being provided to server(s) 730 and/or BEDS device(s) 740 via a user interface. As another example, where a wearer's collected physiological parameter data and health state data are uploaded to a cloud computing network for trend analysis by a clinician, the data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined.

Additionally or alternatively, wearers of a device may be provided with an opportunity to control whether or how the device collects information about the wearer (e.g., information about a user's medical history, social actions or activities, profession, a user's preferences, or a user's current location), or to control how such information may be used. Thus, the wearer may have control over how information is collected about him or her and used by a clinician or physician or other user of the data. For example, a wearer may elect that data, such as health state and physiological parameters, collected from his or her device may only be used for generating an individual baseline and recommendations in response to collection and comparison of his or her own data and may not be used in generating a population baseline or for use in population correlation studies.

Figure 8A:
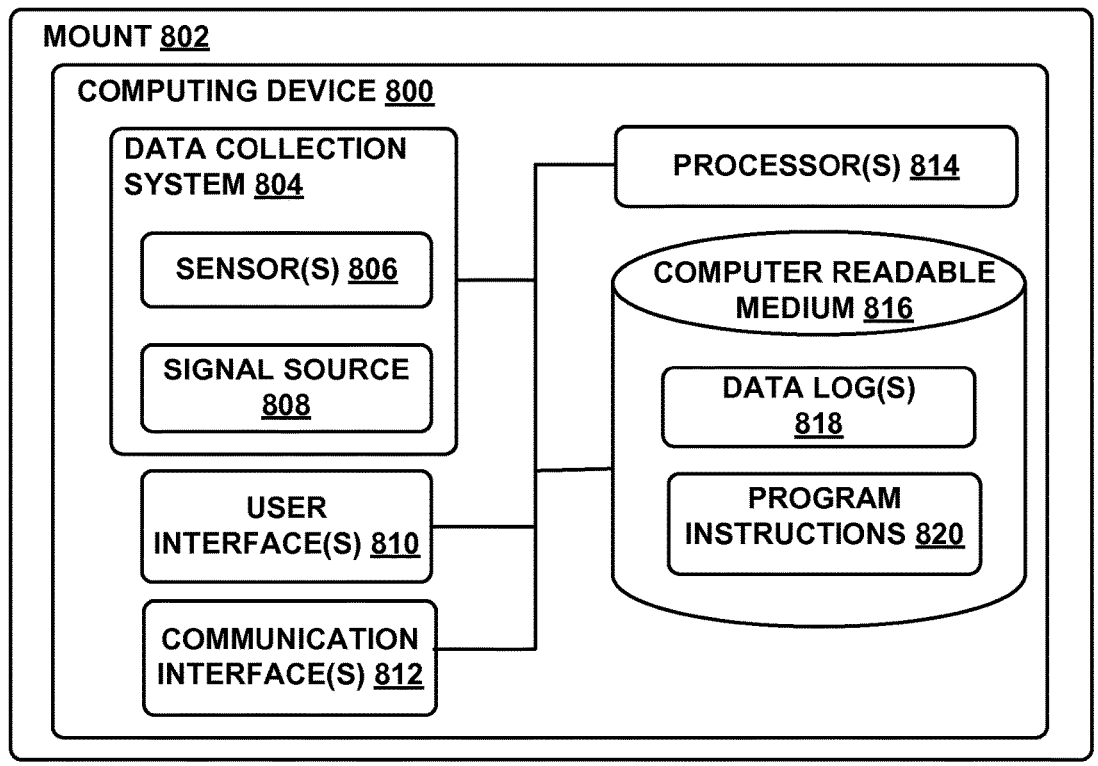
FIG. 8A is a functional block diagram of an example computing device, in accordance with an example embodiment.

FIG. 8A is a functional block diagram of example computing device 800, in accordance with an example embodiment. Computing device 800 may be configured to carry out some or all of the herein-described functionality of wrist-mounted devices 200, 300, 400, 500, 600, wearable devices 700, 702, 704, associated computing device 716, server(s) 730, BEDS device(s) 740, and/or data sources 750, 752, 754, 756, 758, 760 shown in the Figures. However, computing device 800 may also take other forms, such as, but not limited to, an ankle-mountable device, a waist-mountable device, a chest-mountable device, a head-mountable device, a laptop computing device, a tablet computing device, a smart phone, or an immobile computing device.

In particular, FIG. 8A shows an example of a computing device 800 having a data collection system 804, a user interface 810, communication interface(s) 812, processor(s) 814, and computer-readable medium 816. The components of the computing device 800 can be disposed on mount 802 for mounting the device to an external body surface or other surface. In some embodiments, computing device 800 can be deployed without mount 802.

Processor(s) 814 can be one or more general-purpose processors and/or special purpose processors (e.g., digital signal processors, application specific integrated circuits, graphics processing units, etc.). Processor(s) 814 can be configured to execute computer-readable program instructions 820 stored in the computer readable medium 816, where program instructions 820 are executable by processor(s) 814 to provide and/or facilitate some or all the functionality described herein, including but not limited to, the functionality of a wrist-mounted device wearable device, associated computing device, data source, server, and/or BEDS device described herein. Computer readable medium 816 may further contain other data or information usable provide the functionality described herein, including but not limited to, the functionality of a wearable device, associated computing device, and/or server described herein. For example, as shown in FIG. 8A, computer readable medium 816 can store physiological and/or other biological data obtained by computing device 800, as well as other data. In some embodiments, some or all of the data stored computer readable medium 816 can be stored in data log(s) 818; for example, a data log of data log(s) 818 can store physiological and/or other biological data.

Computer readable medium 816 may include or take the form of one or more non-transitory, computer-readable storage media that can be read or accessed by at least one processor 814. The one or more computer-readable storage media can include volatile and/or non-volatile storage components, such as optical, magnetic, organic, electronic, flash, or other memory or disc storage, which can be integrated in whole or in part with at least one of processor(s) 814. In some embodiments, the computer readable medium 816 can be implemented using a single physical device (e.g., one optical, magnetic, organic, electronic, flash, or other memory or disc storage unit), while in other embodiments, the computer readable medium 816 can be implemented using two or more physical devices.

FIG. 8A shows that data collection system 804 includes sensor(s) 806 and, in some embodiments, a signal source 808. Signal source 808 may generate an interrogation signal, timing signal, and/or other signal that will produce a responsive signal that can be detected by one or more of sensor(s) 806.

Sensor(s) 806 may include any sensor and/or detector capable of detecting at least one physiological parameter, which could include any parameters that may relate to the health of the person wearing the wearable device. For example, sensor(s) 806 could include one or more detectors and/or sensors configured to measure physiological data, such as blood pressure, pulse rate, skin temperature, etc. In some examples, one or more of sensor(s) 806 is configured to non-invasively measure one or more analytes in blood circulating in subsurface vasculature proximate to the wearable device. In some embodiments, sensor(s) 806 may include one or more of an optical (e.g., CMOS, CCD, photodiode), acoustic (e.g., piezoelectric, piezoceramic), electrochemical (voltage, impedance), thermal, mechanical (e.g., pressure, strain), magnetic, or electromagnetic (e.g., magnetic resonance) sensor.

In some embodiments, sensor(s) 806 may include one or more sensors and/or detectors configured to measure conditions in an environment about computing device 800 and provide data about that environment. The data can include, but is not limited to: data about computing device 800, location data about computing device 800, velocity (speed, direction) data about computing device 800, acceleration data about computing device 800, and other data about the environment for computing device 800. Examples of sensor(s) 806 configured to measure conditions in an environment include, but are not limited to, power sensor(s), battery sensor(s), movement sensor(s), GPS sensor(s), location sensors(s), gyroscope(s), accelerometer(s), magnetometer(s), camera(s), light sensor(s), infrared sensor(s), and microphone(s).

User interface 810 may be operable to send data to and/or receive data from external user input/output devices. For example, user interface 810 can be configured to send and/or receive data to and/or from user input devices such as a keyboard, a keypad, a touch screen, a computer mouse, a track ball, a joystick, a camera, a voice recognition module, and/or other similar devices. User interface 810 can also be configured to provide output to user display devices, such as one or more cathode ray tubes (CRT), liquid crystal displays (LCDs), light emitting diodes (LEDs), displays using digital light processing (DLP) technology, printers, light bulbs, and/or other similar devices, either now known or later developed. User interface 810 can also be configured to generate audible output(s), such as a speaker, speaker jack, audio output port, audio output device, earphones, and/or other similar devices. In some embodiments, user interface 810 can be configured to generate haptic output(s), such as vibrations and/or other outputs detectable by touch and/or physical contact with computing device 800.

Communication interface 830 of computing device 800 can be utilized for sending and/or receiving information. Communications interface 830 can include a wireless interface and/or a wired interface, which can be disposed on or in computing device 800. The wireless interface can include one or more antennas, wireless transmitters, wireless receivers, and/or wireless transceivers, such as a Bluetooth transceiver, a Zigbee transceiver, a Wi-Fi transceiver, a WiMAX transceiver, and/or other similar type of wireless transceiver configurable to communicate via a wireless network. The wired interface of communications interface 830 can include one or more wireline transmitters, receivers, and/or transceivers, such as a Universal Serial Bus (USB) transceiver, an Ethernet transceiver, and/or similar transceiver configurable to communicate via a twisted pair wire, a coaxial cable, a fiber-optic link, or a similar physical connection to a wired network. The communication interface 830 can optionally include one or more oscillators, mixers, frequency injectors, etc. to modulate and/or demodulate information on a carrier frequency to be transmitted and/or received by the wireless interface. In some examples, the wearable device 800 is configured to indicate an output from the processor by modulating an impedance of the antenna in a manner that is perceivable by a remote server or other remote computing device.

Figure 8B:
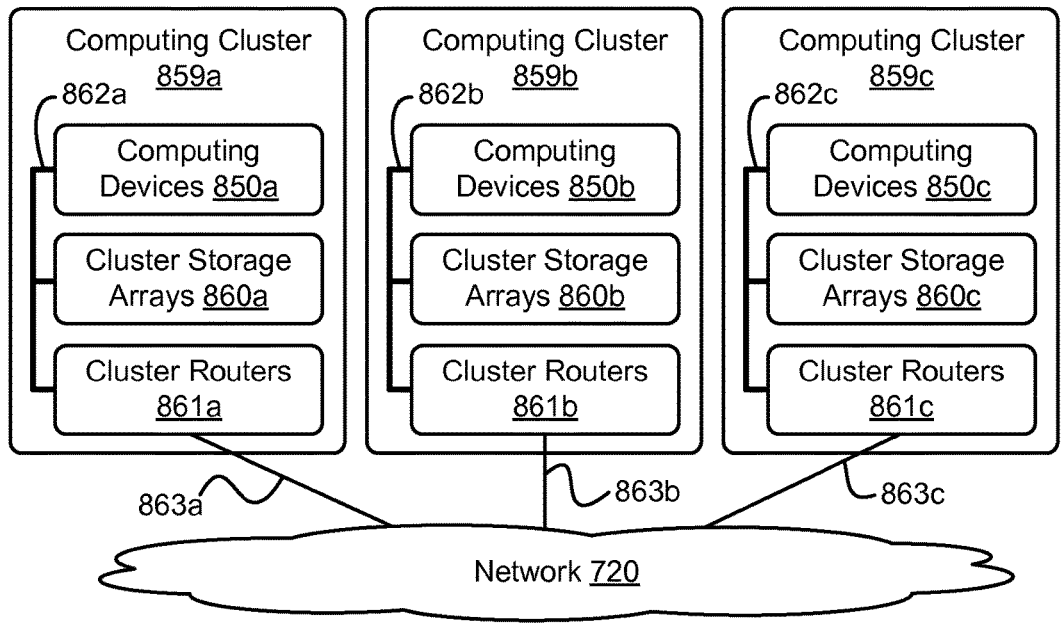
FIG. 8B depicts a cloud-based server system, in accordance with an example embodiment.

FIG. 8B depicts a cloud-based server system, in accordance with an example embodiment. FIG. 8B depicts a network 720 of computing clusters 859a, 859b, 859c arranged as a cloud-based server system in accordance with an example embodiment. Server(s) 730 and/or BEDS device(s) 740 can be cloud-based devices that store program logic and/or data of cloud-based applications and/or services. In some embodiments, server(s) 730 and/or BEDS device(s) 740 can be a single computing device residing in a single computing center. In other embodiments, server(s) 730 and/or BEDS device(s) 740 can include multiple computing devices in a single computing center, or even multiple computing devices located in multiple computing centers located in diverse geographic locations. For example, FIG. 7 depicts server(s) 730 and/or BEDS device(s) 740 residing in different physical locations.

In some embodiments, data and services at server(s) 730 and/or BEDS device(s) 740 can be encoded as computer readable information stored in non-transitory, tangible computer readable media (or computer readable storage media) and accessible by programmable devices 700, 702, 704, associated computing device 716, communications networks 720, data sources 750-760, and/or other computing devices. In some embodiments, data at server(s) 730 and/or BEDS device(s) 740 can be stored on a single disk drive or other tangible storage media, or can be implemented on multiple disk drives or other tangible storage media located at one or more diverse geographic locations.

In FIG. 8B, the functions of server(s) 730 and/or BEDS device(s) 740 can be distributed among three computing clusters 859a, 859b, and 859c. Computing cluster 859a can include one or more computing devices 850a, cluster storage arrays 860a, and cluster routers 861a connected by a local cluster network 862a. Similarly, computing cluster 859b can include one or more computing devices 850b, cluster storage arrays 860b, and cluster routers 861b connected by a local cluster network 862b. Likewise, computing cluster 859c can include one or more computing devices 850c, cluster storage arrays 860c, and cluster routers 861c connected by a local cluster network 862c.

In some embodiments, each of the computing clusters 859a, 859b, and 859c can have an equal number of computing devices, an equal number of cluster storage arrays, and an equal number of cluster routers. In other embodiments, however, each computing cluster can have different numbers of computing devices, different numbers of cluster storage arrays, and different numbers of cluster routers. The number of computing devices, cluster storage arrays, and cluster routers in each computing cluster can depend on the computing task or tasks assigned to each computing cluster.

In computing cluster 859a, for example, computing devices 850a can be configured to perform various computing tasks of electronic communications server 862. In one embodiment, the various functionalities of electronic communications server 862 can be distributed among one or more of computing devices 850a, 850b, and 850c. Computing devices 850b and 850c in computing clusters 859b and 859c can be configured similarly to computing devices 850a in computing cluster 859a. On the other hand, in some embodiments, computing devices 850a, 850b, and 850c can be configured to perform different functions.

In some embodiments, computing tasks and stored data associated with server(s) 730 and/or BEDS device(s) 740 can be distributed across computing devices 850a, 850b, and 850c based at least in part on the processing requirements of server(s) 730 and/or BEDS device(s) 740, the processing capabilities of computing devices 850a, 850b, and 850c, the latency of the network links between the computing devices in each computing cluster and between the computing clusters themselves, and/or other factors that can contribute to the cost, speed, fault-tolerance, resiliency, efficiency, and/or other design goals of the overall system architecture.

The cluster storage arrays 860a, 860b, and 860c of the computing clusters 859a, 859b, and 859c can be data storage arrays that include disk array controllers configured to manage read and write access to groups of hard disk drives. The disk array controllers, alone or in conjunction with their respective computing devices, can also be configured to manage backup or redundant copies of the data stored in the cluster storage arrays to protect against disk drive or other cluster storage array failures and/or network failures that prevent one or more computing devices from accessing one or more cluster storage arrays.

Similar to the manner in which the functions of server(s) 730 and/or BEDS device(s) 740 can be distributed across computing devices 850a, 850b, and 850c of computing clusters 859a, 859b, and 859c, various active portions and/or backup portions of these components can be distributed across cluster storage arrays 860a, 860b, and 860c. For example, some cluster storage arrays can be configured to store the data of server(s) 730, while other cluster storage arrays can store data to act as BEDS device(s) 740. Additionally, some cluster storage arrays can be configured to store backup versions of data stored in other cluster storage arrays.

The cluster routers 861a, 861b, and 861c in computing clusters 859a, 859b, and 859c can include networking equipment configured to provide internal and external communications for the computing clusters. For example, the cluster routers 861a in computing cluster 859a can include one or more internet switching and routing devices configured to provide (i) local area network communications between the computing devices 850a and the cluster storage arrays 860a via the local cluster network 862a, and (ii) wide area network communications between the computing cluster 859a and the computing clusters 859b and 859c via the wide area network connection 863a to network 720. Cluster routers 861b and 861c can include network equipment similar to the cluster routers 861a, and cluster routers 861b and 861c can perform similar networking functions for computing clusters 859b and 859c that cluster routers 861a perform for computing cluster 859a.

In some embodiments, the configuration of the cluster routers 861a, 861b, and 861c can be based at least in part on the data communication requirements of the computing devices and cluster storage arrays, the data communications capabilities of the network equipment in the cluster routers 861a, 861b, and 861c, the latency and throughput of local networks 862a, 862b, 862c, the latency, throughput, and cost of wide area network links 863a, 863b, and 863c, and/or other factors that can contribute to the cost, speed, fault-tolerance, resiliency, efficiency and/or other design goals of the moderation system architecture.

Example Methods of Operation

Figure 9:
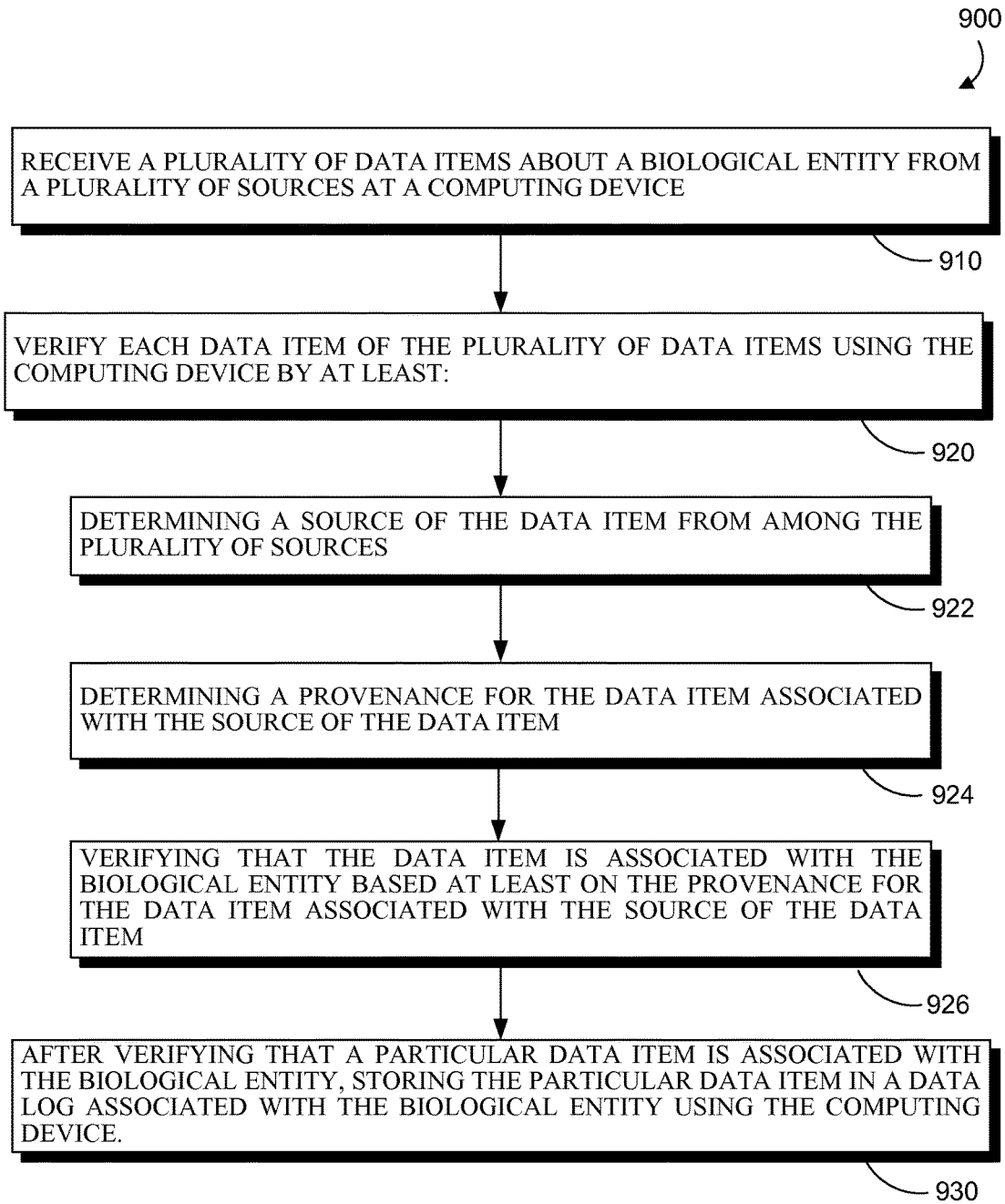
FIG. 9 is a flowchart of an example method of storing data at a computing device, in accordance with an example embodiment.

FIG. 9 is a flowchart of a method 900 storing data at a computing device. Example computing devices include, but are not limited to, herein-described computing device 800, wearable devices, associated computing devices, servers, BEDS devices, and data sources.

Method 900 can begin at block 910, where a computing device can receive a plurality of data items about a biological entity from a plurality of sources.

In some embodiments, the plurality of sources can include a wearable device being worn by the biological entity. Then, the plurality of data items can include a data item that includes physiological data obtained by one or more sensors of the wearable device. The physiological data can include, for example, cardiac data (e.g., pulse rate, blood pressure), pulmonary data (breathing rate), and/or analyte data (e.g., the concentration of an analyte in blood, tears, perspiration, or other body fluid).

In other embodiments, the plurality of data items can include at least one data item selected from the group of data items consisting of: a data item about an environment of the biological entity, a data item about a physiological measurement of the biological entity, a data item about a mood of the biological entity, and a data item related to demographical information related to the biological entity.

At block 920, the computing device can verify each data item of the plurality of data items using the computing device by at least carrying out the procedures of blocks 922, 924, and 926.

At block 922, the computing device can determine a source of the data item from among the plurality of sources.

At block 924, the computing device can determine a provenance for the data item associated with the source of the data item.

At block 926, the computing device can verify that the data item is associated with the biological entity based at least on the provenance for the data item associated with the source of the data item.

In some embodiments, verifying that the data item is associated with the biological entity can include determining whether the wearable device is being worn by the biological entity based on the provenance for the data item.

In other embodiments, the provenance of the data item can include a network address associated with the source.

At block 930, after verifying that a particular data item is associated with the biological entity, the computing device can store the particular data item in a data log associated with the biological entity.

In some embodiments, storing the particular data item in the data log can include: storing a data record for the particular data item in the data log. The data record can include data about an entity providing the particular data item, data about a time associated with the particular data item, and data about a type of the particular data item. In particular of these embodiments, the type of the particular data item can include a type of activity associated with the particular data item. In other particular of these embodiments, the type of the particular data item can include a type of physiological measurement associated with the particular data item.

In other embodiments, storing the particular data item can include storing the particular data item in two or more physical locations, such as discussed below in the context of at least FIG. 15.

Figure 13:
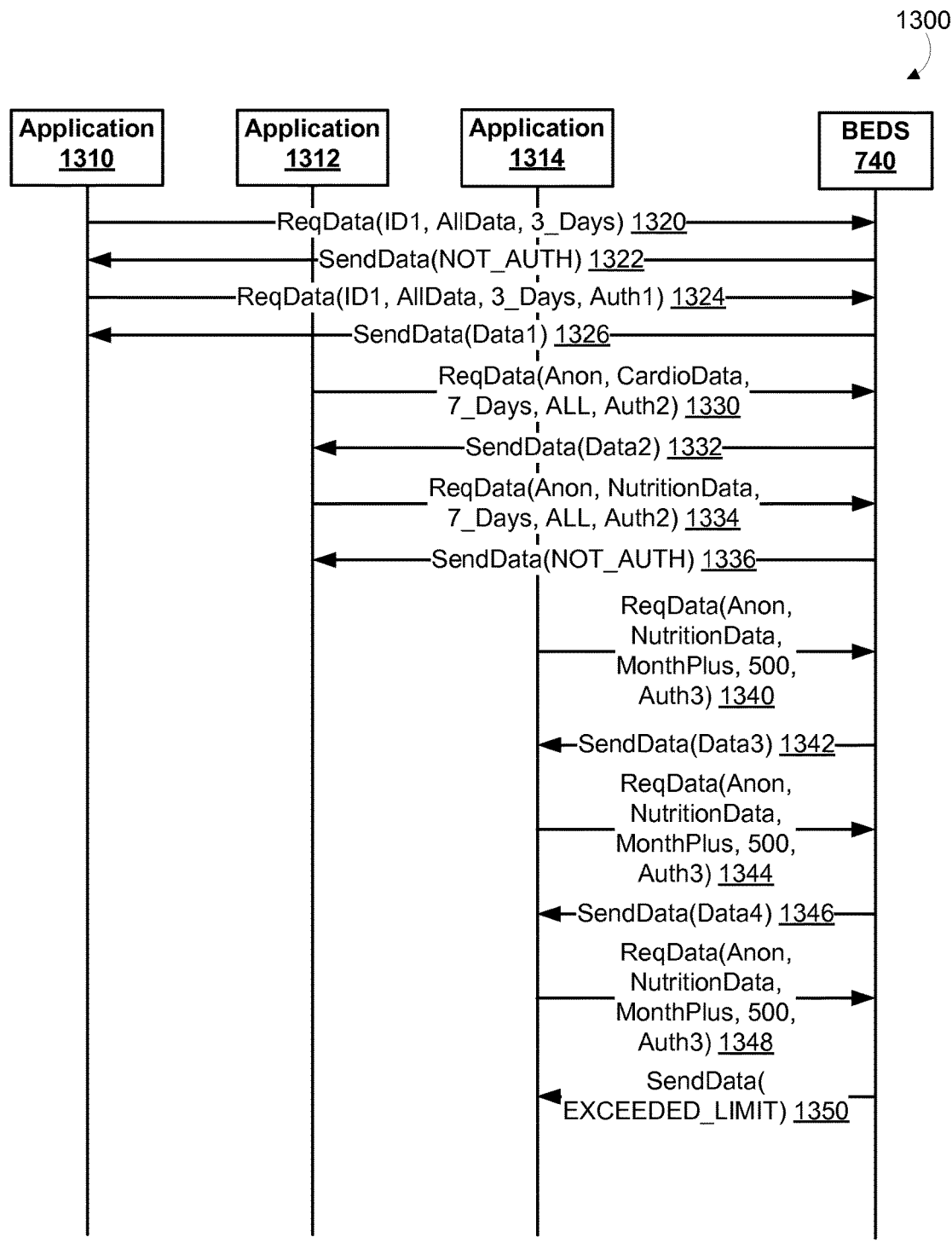
FIG. 13 depicts an example scenario for data retrieval, in accordance with an example embodiment.

In some embodiments, method 900 can further include: requesting a portion of data stored in the data log, where the request can be configured to indicate whether to include identifying information about biological entities associated with the requested portion of data; and, after determining that the request is configured to indicate not to include identifying information about biological entities associated with the requested portion of data, providing the requested portion of data stored in the data log without the identifying information about the associated biological entities, such as discussed below in the context of at least FIG. 13.

Example Permission Schemes and Data Sharing for Wearable Devices

Figure 10:
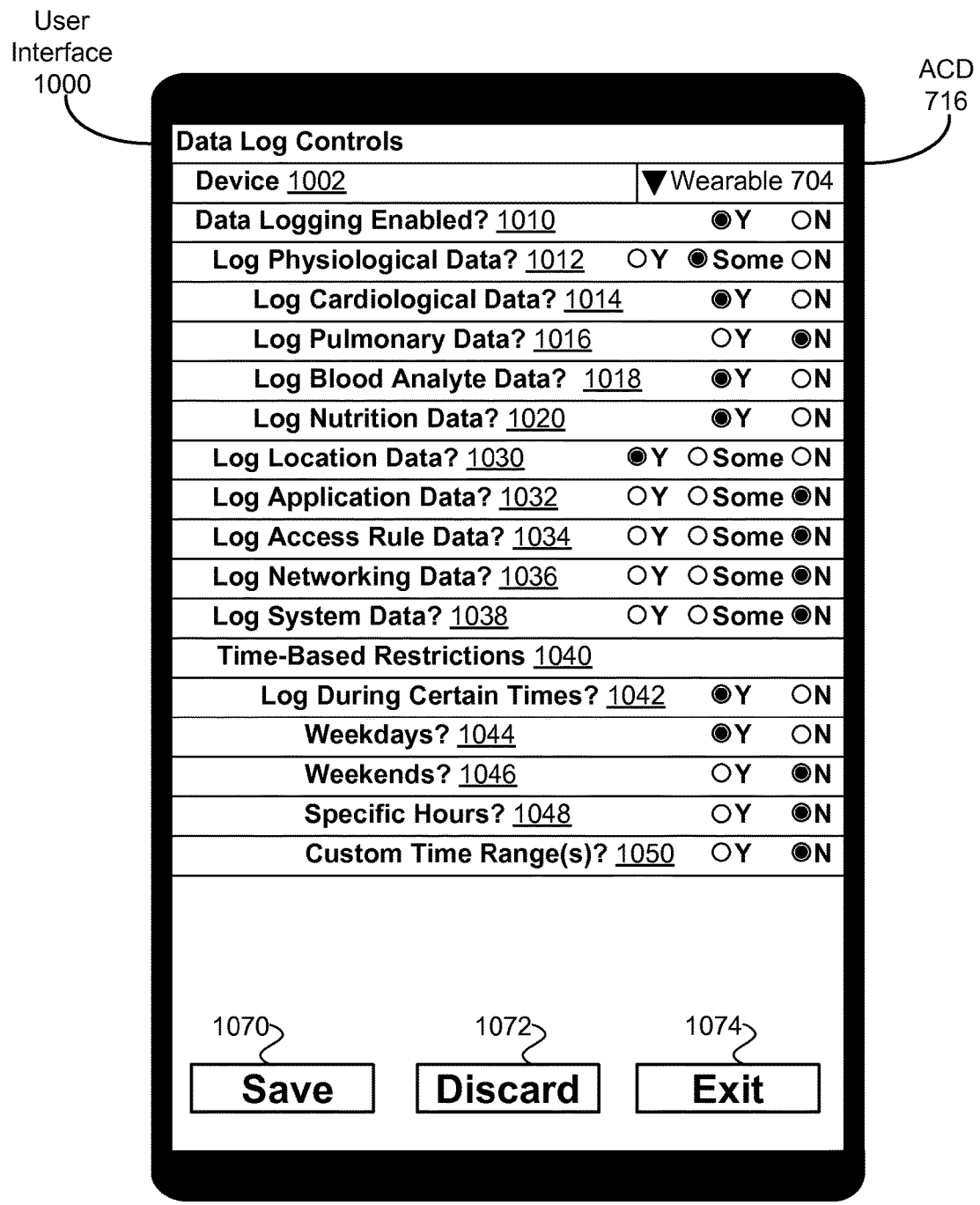
FIG. 10 depicts an example user interface for controlling data logging, in accordance with an example embodiment.

FIG. 10 depicts an example user interface 1000 for controlling data logging. User interface 1000 is shown being utilized on associated computing device (ACD) 716. In other embodiments, some or all of the herein-described functionality of user interface 1000, can be provided on a wearable device, a server, BEDS device, data source, and/or on one or more other computing devices. User interface 1000 includes an interface for specifying whether, and perhaps which, types of data are to be logged; e.g., logged remotely on BEDS device(s) 740. In some embodiments, only the wearer of a wearable device associated with associated computing device 716; i.e., the wearer of wearable device 704, can utilize user interface 1000. In some embodiments, user interface 1000 can only be utilized by an entity having an appropriate role; e.g., a role enabling access to control data for data logging.

Device control 1002 can enable selection of a device for controlling data logging; e.g., in a scenario where associated computing device 716 is connected to wearable device 704 as shown in 704, device control 1002 may enable selection of wearable device 704 or associated computing device 716. Then, when device control 1002 is set to "Wearable 704" as shown in FIG. 10, then the data log control settings can be applicable for wearable device 704.

As shown in FIG. 10, data log controls can include "Data Logging Enabled" control 1010, "Log Physiological Data" control 1012, "Log Location Data" control 1030, "Log Application Data" control 1032, "Log Access Rule Data" control 1034, "Log Networking Data" control 1036, and "Log System Data" control 1038.

In the example interface 1000 for controlling data logging, selecting a "Y" for Yes indicates a type of data is to be remotely logged for a selected device that can be selected by device control 1002, selecting a "N" for No indicates the type of data is not to be remotely logged for the selected device, and selecting a "Some" indicates that some of the data is to be remotely logged for the selected device.

"Data Logging Enabled" control 1010 controls whether or not remote data logging is performed at all for the device selected by device control 1002. That is, if data logging control 1010 is set to "N", then no data logging is performed for the selected device. As shown in FIG. 10, "Data Logging Enabled" control 1010 is set to "Y", indicating data logging for the selected device "Wearable 704" is enabled.

Data for controlling data logging; i.e., the data log controls managed by user interface 1000, can be stored in a number of locations. Example locations include, but are not limited to one or more wearable devices, associated computing devices, servers, and/or other computing devices. In some embodiments, one or more remote data logging devices can be selected, perhaps using an IP address or partially qualified domain name; e.g., log all data to "0.1.2.3", "beds_device1.remote_logging_of_data_for_me.com", any or all devices at "remote_logging_of_data_for_me.com". Other techniques for specifying remote data logging devices are possible as well. In still other embodiments, different types of data can be logged to different devices; e.g., physiological data can be logged to a first remote device, and application data can be logged to a second remote device, where the first and second remote devices differ.

Each control 1012, 1030, 1032, 1034, 1036, 1038 can permit selection for allowing, partially allowing, or disabling logging of a respective type of data; e.g., "Log Physiological Data" control 1012 permits selection for allowing, partially allowing, or disabling logging of physiological data. When one of controls 1012, 1030, 1032, 1034, 1036, 1038 is set to "Y", then all data having the respective type of data for the selected device is remotely logged. For example, FIG. 10 shows "Log Location Data" control 1030 is set to "Y", indicating that all location data for the selected device "Wearable 704" is to be remotely logged.

When one of controls 1012, 1030, 1032, 1034, 1036, 1038 is set to "N", then no data having the respective type of data for the selected device is remotely logged. For example, FIG. 10 shows that each of "Log Application Data" control 1032, "Log Access Rule Data" control 1034, "Log Networking Data" control 1036, and "Log System Data" control 1038 are set to "N". Then, as "Log Application Data" control 1032 is set to "N", no application data, such as data generated by and/or provided to an application of the selected device is to be remotely logged. Also, as "Log Access Rule Data" control 1034 is set to "N", no access rule data, such as access rules controlling utilizing of data on the selected device, is to be remotely logged. Further, as "Log Networking Data" control 1036 is set to "N", networking data is not logged. Also, as Log System Data" control 1038 is set to "N", no data specifically used by the systems controlling the selected device is to be remotely logged.

When one of controls 1012, 1030, 1032, 1034, 1036, 1038 is set to "Some", additional logging controls for sub-types of the selected type of data can be provided by user interface 1010. For example, FIG. 10 shows that "Log Physiological Data" control 1012 is set to "Some". In response, user interface 1012 displays "Log Cardiological Data" control 1014, "Log Pulmonary Data" control 1016, "Log Blood Analyte Data" control 1018, and "Log Nutrition Data" control 1020 for controlling data logging of four respective sub-types of physiological data. Those respective sub-types are cardiological data, pulmonary data, blood analyte data, and nutrition data. In some embodiments, controls for logging fewer, more, or different controls for logging sub-types of physiological data can be provided.

FIG. 10 shows that Log Cardiological Data" control 1014, "Log Blood Analyte Data" control 1018, and "Log Nutrition Data" control 1020 are each set to "Y", indicating that remote logging of cardiological data, blood analyte data, and nutrition data, respectively, is enabled for the selected device. FIG. 10 also shows that "Log Pulmonary Data" control 1016 is set to "N", indicating that remote logging of pulmonary data is not enabled.

Settings 1044, 1046, 1048, and 1050 provide various settings for specifying time-based restrictions settings on data logging. Settings 1044 and 1046 allow control for remotely logging data generated by the selected device during weekdays and weekends, respectively. Setting 1048 allows control for remotely logging data generated by the selected device during specific hours and perhaps days of the week; e.g., log data between 0900 and 1700, log data between 0000 and 0700 on Mondays, Wednesdays, and Fridays. Setting 1050 allows specifying of custom time ranges for remotely logging data generated by the selected device.

Time-based restrictions settings 1040 can control times that data is logged. Setting 1042 controls whether or not any time-based restrictions settings are applicable. If setting 1042 is set to "N", data is logged without any restriction based on time. In other cases, such as shown in FIG. 10, setting 1042 is set to "Y", indicating one or more time-based restrictions settings are applicable.

Settings 1044, 1046, 1048, and 1050 provide various settings for specifying time-based restrictions settings on data logging. Settings 1044 and 1046 allow control for remotely logging data generated by the selected device during weekdays and weekends, respectively. Setting 1048 allows control for remotely logging data generated by the selected device during specific hours and perhaps days of the week; e.g., log data between 0900 and 1700, log data between 0000 and 0700 on Mondays, Wednesdays, and Fridays. Setting 1050 allows specifying of custom time ranges for remotely logging data generated by the selected device.

As shown in FIG. 10, weekdays setting 1044 is set to "Y" to enable logging of data generated during weekdays, weekends setting 1046 is set to "N" to disable logging of data generated during weekends, specific hours setting 1048 is set to "N" to disable specification of specific hours for logging of data, and custom time ranges setting 1050 is set to "N" to disable specification of custom time ranges for data logging. In other embodiments, settings 1044, 1046, 1048, and 1050 can specify one or more times related to when data remotely logged; e.g., times when data is communicated by the selected device, rather than one or more times related to when data is generated by the selected device. Other specifications of time-based restrictions of data logging are possible as well.

As shown in FIG. 10, user interface 1000 also includes three control buttons. "Save" button 1070 can be selected to save any changes made to the data log controls via user interface 1000. "Discard" button 1072 can be selected to not save, or discard, any changes made to the made to the data log controls. "Exit" button 1074 can be selected to exit user interface 1000.

FIG. 11 depicts example data format 1100, in accordance with an example embodiment. Data format 1100 can be used for remotely logging data by a BEDS device, server, and/or by other computing device(s). Data format 1100 can include data independent provenance 1100 about a number N of data items in data format 1100, where N>0. Then, for each of the N data items, a data-dependent provenance and data item can be formatted. For example, FIG. 11 shows that a first data item of data format 1100 has data-dependent provenance 1150a and includes data item 1170a, a second data item of data format 1100 has data-dependent provenance 1150b and includes data item 1170b, and so on. In some examples, a data item may not have a corresponding data-dependent provenance.

In describing data format 1100, let a computing device CD be a computing device storing the data described using data format 1100. For example, data can be provided to a remote-logging device acting as computing device CD; e.g., BEDS device 740, using data format 1100. In other embodiments, data can be provided to the device acting as computing device CD using other data format(s) and then computing device CD can convert or otherwise put any received data into data format 1100.

FIG. 11 shows data-independent provenance 1100 with several fields of information, including number of data items field 1112, data source field 1114, time data received field 1116, data size field 1118, and data type field 1120. In other embodiments, more, fewer, or different fields of information can be part of data-independent provenance 1100. FIG. 11 also shows example default values 1130 for each field of information specified in data-independent provenance 1100.

Number of data items field 1112 can specify a number of data items conveyed using data format 1100 to computing device CD; i.e., number of data items field 1112 is set to the number N discussed above. FIG. 11 also shows example an example default value 1132 of one data item for number of data items field 1112.

Data source field 1114 can specify a source for a data item. For example, if a data item is received from a device named "MyDevice1234" having a fully qualified domain name of "MyDevice1234.google.com" with an internet protocol (IP) address of "1.2.3.4" and a media access control (MAC) address of "a.0.b.0.c.0", data source can be one or more of "MyDevice1234", "MyDevice1234.google.com", "1.2.3.4", and "a.0.b.0.c.0", as well as one or more other identifiers. In some embodiments, data source field 1114 can include a sub-type; e.g., if IP and MAC addresses are both used as data sources, then the above example can have data source field 1114 sub-type of "IP address" (or equivalent) for specifying data source field 1114 as "1.2.3.4" and can have data source field 1114 sub-type of "MAC address" (or equivalent) for specifying data source field 1114 as "a.0.b.0.c.0".

If computing device CD is the source of data, then data source field 1114 can be set to "Self-sourced", "Internal" or an equivalent value; e.g., default value 1134 of "Internal" indicates that the default source for a data item is computing device CD; i.e., the data is self-sourced. In some embodiments, another identifier associated with computing device CD, such as a device name for CD, a fully qualified domain name for CD, an IP address for CD, and/or MAC address for CD, can be used rather than or along with a descriptive term such as "Self-sourced" or "Internal".

Time data received field 1116 can specify a time when data is received at computing device CD, with a default 1136 of "Now"; e.g., the current time. Data size field 1118 can specify an amount of data received at computing device CD; e.g., data size field 1118 can be specified as a number of bits, bytes, kilobytes, megabytes, gigabytes, terabytes, and/or using some other measurement of a data size, with a default value 1138 of <as received>; e.g., the actual size of the data item as calculated or otherwise determined after reception at computing device CD.

Data type field 1120 can specify a data type for received data. In some embodiments, data type field 1120 can specify one or more sub-types as well, while in other embodiments, such as shown in FIG. 11, data sub-types can be specified elsewhere; e.g., as part of data sub-type(s) 1152. Default value 1140 for data type field 1120 is "Unknown"; in other embodiments, other default data types can be used; e.g., for a device storing mainly text, default data type 1140 can be "Text", "Alphanumeric" or equivalent; for a device storing mainly images, default data type 1140 can be "Image", "Video", or equivalent.

As each piece of information in data-independent provenance 1110 has a default value; e.g., default values 1130, a data-independent provenance can be determined for any data item(s) received in any format. That is, data items received in any format can be converted into data format 1110 having at least data-independent provenance 1110. Then, after conversion into data format 1110, data can be logged using techniques based on a provenance for the data item(s) received. Thus, a provenance can be generated or otherwise determined without depending on any specific information being received with the data item(s), allowing processing of the provenance regardless of any or all missing input. Therefore, data received in any format can be logged with data from a provenance, such as provenance 1110 and perhaps one or more of provenances 1150a, 1150b of data format 1100.

Data-dependent provenances, such as data-dependent provenances 1150a, 1150b, can have fields of information that vary based on the type of data. Data sub-type(s) field 1152 can specify one or more sub-types of data, as applicable. For example, data about a pulse rate can be a sub-type of cardiological data, which in turn can be a sub-type of physiological data. In some embodiments, data type field 1118 can specify sub-type(s) as well; e.g., for data of type "physiological data", a sub-type can be "blood analyte reading" and example sub-sub-types can be "glucose reading", "sodium reading", "carbon dioxide reading", etc.

Location field 1154 can specify a location where data is collected; e.g., a set of latitude/longitude or latitude/longitude/altitude coordinates; other data from a location device, such as but not limited to a GPS sensor, a physical (street, mailing) address. In some embodiments, data in a data-dependent provenance can include the data being conveyed; e.g., during logging of location data, location field 1154 can be both part of a provenance for a data item as well as part of or the entire data item. In some embodiments, other types of locations can be used; e.g., network addresses, road intersections (Main St. and $2^{nd}$. Ave.), relative locations (e.g., 1 mile east of the Jones ranch), and/or locations specified in other coordinate systems.

Associated entity ID field 1156 can identify an entity associated with a data item; e.g., for physiological data, the associated entity can identify a wearer (or other biological entity) associated with the physiological data. For example, associated entity ID field 1156 can be a name, identifying number (e.g., Social Security number, account number, driver's license number, passport number, credit card number, employee ID number), and/or other identifier associated with a wearer. In some embodiments, associated entity ID field 1156 can be verified based on other data items in a provenance; e.g., if associated entity ID field 1156 is "Pat Smith", where Pat Smith the name of a wearer named that has previously provided most (or all) data to computing device CD using a particular device D1, then when data source field 1114 refers to device D1, the reference to D1 can partially or completely verify Pat Smith is indeed the entity associated with the data item. Other provenance data, such as location field 1154, time data received field 1158, sensor information in provenance fields 1162 and 1164, as well as other provenance data, can be used to partially or completely verify whether an entity specified via is associated entity ID field 1156 actually associated with a data item.

Entity providing data field 1158 can identify an entity providing the data. For example, if a device D2 receives data DD1 from another device D3 via the Internet (or another network), D3 can be specified as the entity in entity providing data field 1158 for data item(s) associated with data DD1.

Time data generated field 1160 can specify a time when data is generated. In some cases, the time data is received by computing device CD is very nearly the same as when the data is generated; in these cases, time data generated field 1160 may be unspecified, ignored, and/or time data received field 1116 can act as a proxy for time data generated field 1160. In other cases, data can be provided to computing device CD after a delay; e.g., to guard against privacy concerns related with very recent location and/or other sensitive data. In these cases, the data can be provided with time data generated field 1160 information for logging purposes once enough time has elapsed to ameliorate security concerns.

Sensor data fields, such as a type of sensor used to generate data field 1162 and/or additional sensor information field 1164, can be provided for data obtained and/or processed using sensors. Additional sensor information field 1164 can include, but is not limited to, sensor manufacturer information, sensor name information, sensor model number(s), sensor hardware, software, and/or other version information, valid (and/or invalid) ranges of sensor data, diagnostic information about the sensor, and valid (and/or invalid) conditions for operating the sensor. Additional information about data field 1166 can include any other information about one or more data items.

In some cases, some or all of the fields in a data-dependent provenance, such as fields in data-dependent provenances 1150a, 1150b, can have default values. Then, if data is known to utilize a data-dependent provenance having a default value for each piece of information in the provenance, a data-dependent provenance can be generated or otherwise determined without any specific information being received with the data, allowing processing of the data-dependent provenance regardless of any or all missing input.

More, less, and/or different fields of information are possible for a data-dependent provenance. In some embodiments, a data-dependent provenance can include all of the fields of information in a data-independent provenance; e.g., provenances 1110 and 1150a can be merged into a single provenance for data item 1170a.

Figure 12:
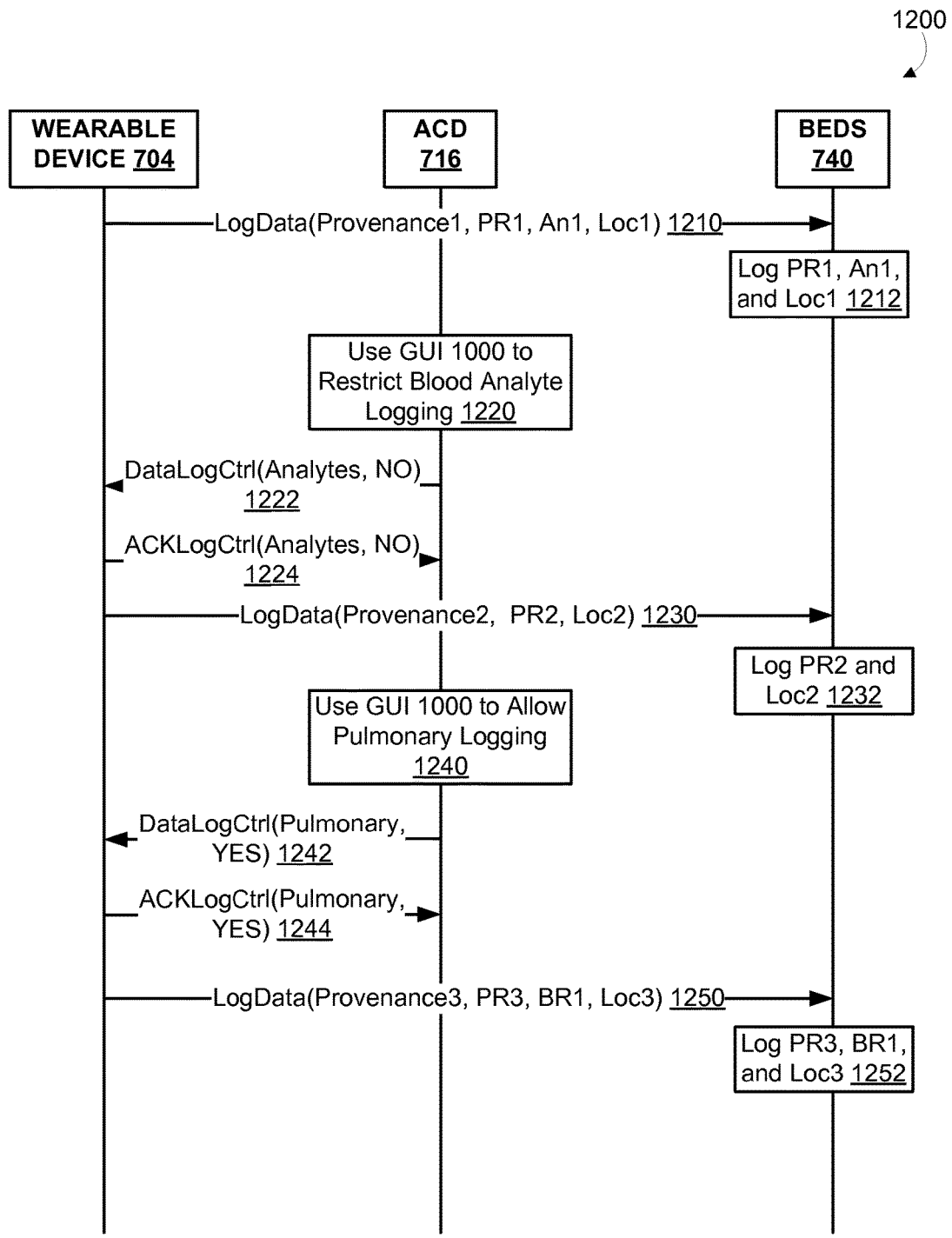
FIG. 12 depicts an example scenario for data logging, in accordance with an example embodiment.

FIG. 12 depicts an example scenario 1200 for data logging, in accordance with an example embodiment. Scenario 1200 involves data being logged from wearable device 704 on BEDS device 740 during a weekday. At the onset of scenario 1200, data is logged from wearable device 704 in accord with the settings of user interface 1000 as shown in FIG. 10; e.g., all location data and some physiological data is logged, while other types of data are not enabled for logging, and data is logged only during weekdays. Each of FIGS. 12, 13, and 14 do not indicate when data traverses intermediate devices; e.g., data from wearable device 704 sent to BEDS device 740 is not shown as perhaps being received and then retransmitted by associated computing device 716 and/or communication network(s) 720.

Example scenario 1200 involves devices 704, 716 providing data to server(s) 730 and BEDS device(s) 740 for logging, and the data is then logged (stored) on BEDS device(s) 740. In scenario 1200, the logging is silent; that is, no acknowledgement of received data is provided by server(s) 730 and/or BEDS device(s) 740. In other scenarios, server(s) 730 and/or BEDS device(s) 740 can provide acknowledgments for received data.

Scenario 1200 begins with wearable device 704 generating and sending LogData message 1210 to provide three data items to BEDS device 740: pulse rate data PR1, blood analyte data AN1, and location data Loc1. The three data items are provided with one or more provenances Provenance1. Provenance1 and other provenances discussed in scenario 1200 can include one or more of the provenances discussed in context of FIG. 11, other provenances, and/or provenance-related information. For example, Provenance1, Provenance2, and/or Provenance3 can include a data-independent provenance, such as provenance 1110, a data-dependent provenance, such as provenance 1150, and/or another provenance-related information; e.g., information that can act as (or lead to generation of) a provenance, such as packet header information and/or metadata provided with the LogData message 1210.

At block 1212, BEDS device 740 can obtain data items PR1, AN1, and Loc1 from LogData message 1210 and store the data items, along with data from Provenance1. For example, BEDS device 740 can store the data items and associated provenance information in a log file associated with a wearer of wearable device 704 whose pulse rate and blood analyte data were respectively recorded as PR1 and AN1 and who was at (or near) location Loc1. BEDS device 740 can store the data items using a data format, such as data format 1100. For example, BEDS device 740 can store data items in one or more data records, where each data record contains values of one or more fields of information. The data record can include values for received data items, as well as values for fields in one or more provenances; e.g., one or more data-independent provenances and/or one or more data-dependent provenances.

In scenario 1200, Provenance1 of LogData message 1210 includes information to specify each data field in data-independent provenance 1100 for each of data items PR1, AN1, and Loc1, but does not contain any data-dependent information. Then, BEDS device 740 can store the data items; e.g., as indicated in example log record of Table 1 below (data sizes specified in bytes).

TABLE 1

Data Source: Wearable Device 704
Time Data Received: 18:00:00 UTC 29 May 2014
Number of Data Items: 3
Data Size for Data Item 1: 2
Data Type for Data Item 1: Pulse Rate
Data Value for Data Item 1: 120
Data Size for Data Item 2: 4
Data Type for Data Item 2: Blood Analyte Value
Data Value for Data Item 2: 3.6
Data Size for Data Item 3: 8
Data Type for Data Item 3: Location (Lat/Long)
Data Value for Data Item 3: 41.919201 −87.628763

Scenario 1200 continues at block 1220 with the wearer of wearable device 704 using user interface 1000 of associated computing device 716 to change data logging permissions for wearable device 704 to restrict future blood analyte logging. For example, the wearer can instruct associated computing device 716 to display user interface 1000, set blood analyte data logging control 1018 to N, and then save the data logging controls using save button 1070.

After the wearer has restricted future blood analyte data logging, associated computing device 716 can send Data-LogCtrl message 1222 to instruct wearable device 704 to no longer provide blood analyte data for remote logging. In response, wearable device 704 can record the instruction to no longer provide blood analyte data for remote logging, and send an acknowledgement ACKLogCtrl message 1224 to acknowledge DataLogCtrl message 1222. Like DataLogCtrl message 1222, ACKLogCtrl message 1224 includes two parameters: a type of log control parameter shown as "Analyte" in the examples shown for messages 1222 and 1224, and a log control setting parameter shown as "N" in the examples shown for messages 1222 and 1224. ACK-LogCtrl message 1224 can include a copy of the parameters provided in DataLogCtrl message 1222 to indicate which log control parameters and their respective settings have been received and so updated by wearable device 704. In other scenarios, wearable device 704 can record the instruction to no longer provide blood analyte data without sending an acknowledgement message.

In scenario 1200, data logging of wearable device 704 is performed at periodic time intervals; e.g., a log message is sent every minute. In other scenarios, data logging can be performed based on other conditions than expiration of a time interval; e.g., when data is available, upon request by a wearer or other entity, when a buffer storing logging data is near or at capacity. In still other scenarios, some or all conditions where data logging is performed can be controlled via a user interface; e.g., user interface 1000.

In accord with periodic data logging, scenario 1200 continues with wearable device 704 generating and sending LogData message 1230 to BEDS device 740. LogData message 1230 includes data provenance Provenance2 and two data items: pulse rate data PR2 and location data Loc2. In comparison with LogData message 1210, no blood analyte data information is provided with LogData message 1230, in accord with the data logging control to restrict blood analyte data logging provided in DataLogCtrl message 1222.

At block 1232, BEDS device 740 can obtain data items PR2 and Loc2 from LogData message 1230 and store the data items, along with data from Provenance2, using the techniques discussed above in the context of block 1212.

Scenario 1200 continues at block 1240 with the wearer of wearable device 704 using user interface 1000 of associated computing device 716 to enable future pulmonary data logging. For example, the wearer can instruct associated computing device 716 to display user interface 1000, set pulmonary data logging control 1016 to Y, and then save the data logging controls using save button 1070.

After the wearer has allowed future pulmonary data logging, associated computing device 716 can send Data-LogCtrl message 1242 to instruct wearable device 704 to provide pulmonary data for remote logging. In response, wearable device 704 can record the instruction to no longer provide blood analyte data for remote logging, and send an acknowledgement ACKLogCtrl message 1244 to acknowledge DataLogCtrl message 1242. FIG. 12 shows that Data-LogCtrl message 1242 and ACKLogCtrl message 1244 both have a type of log control parameter set to "Pulmonary" in FIG. 10 and a log control setting parameter set to "Y".

In accord with periodic data logging, scenario 1200 continues with wearable device 704 generating and sending LogData message 1250 to BEDS device 740. LogData message 1250 includes data provenance Provenance3 and three data items: pulse rate data PR3, breathing rate data BR1, and location data Loc2. In comparison with LogData message 1210, no blood analyte data information is provided with LogData message 1250, in accord with the data logging control to restrict blood analyte data logging provided in DataLogCtrl message 1222. Further, in comparison with LogData messages 1210 and 1230, pulmonary information, in the form of breathing rate data BR1, is provided with LogData message 1250, in accord with the data logging control to enable pulmonary data logging provided in DataLogCtrl message 1242.

At block 1252, BEDS device 740 can obtain data items PR3, BR1, and Loc3 from LogData message 1250 and store the data items, along with data from Provenance3, using the techniques discussed above in the context of block 1212. BEDS device 740 can store the data items in example log record of Table 2 below (data sizes specified in bytes).

TABLE 2

Data Source: Wearable Device 704
Time Data Received: 18:02:00 UTC 29 May 2014
Number of Data Items: 3
Data Size for Data Item 1: 2
Data Type for Data Item 1: Pulse Rate
Data Value for Data Item 1: 65
Data Size for Data Item 2: 2
Data Type for Data Item 2: Breathing Rate
Data Value for Data Item 2: 13
Data Size for Data Item 3: 8
Data Type for Data Item 3: Location (Lat/Long)
Data Value for Data Item 3: 41.922913 −87.629825

After BEDS device 740 has completed the procedures of block 1252, scenario 1200 can then end.

Once data has been logged by server(s) 730 and/or BEDS device(s) 740, logged data can be queried for various purposes; e.g., server(s) 730 and/or BEDS device(s) 740 can receive a query requesting a portion of logged data and, in response, send a query result. If the query is successful, the query result can include the requested portion of logged data. However, if the query is unsuccessful; e.g., the query refers to non-existent and/or unavailable data, then the query result can indicate that the query was unsuccessful.

In some cases, a query can be specific to an entity, such as a specific wearer, or specific device providing data. In other cases, a query can refer to a number of entities; e.g., to determine trends across a population or data set specified by the query. In some cases, data in query results can be anonymized to protect entity information; e.g., identity information of a wearer, location information, information whose dissemination is controlled by privacy laws/standards such as the Health Insurance Portability and Accountability Act (HIPAA).

For example, a query can attempt to verify data based on provenance. For example, data for specific wearer can be verified based on patterns of behavior detected in the data for a wearer; e.g., data sources used to provide data, types of data provided, times that data was provided, data log controls associated with the wearer, and so on. For example, suppose a wearer W only provides logged data from a wearable device WD1 acting as a data source and data from wearable device WD1 is only associated with one wearer, wearer W. Then, data provided from wearable device WD1 can be at least tentatively verified as being from wearer W. Later, wearer W is indicated as providing data from a different wearable device WD2. If other data does not confirm that W is somehow associated with WD2 (e.g., data indicating that W has bought or otherwise obtained WD2), then data associated with both W and WD2 can be determined to be unverified. Similarly, if W provided data only during weekdays, perhaps in accord with time-based restrictions of data logging, data provided on a weekend that is indicated to be associated with W can be determined to be unverified.

A change in location is detected may indicate that data should be unverified. For example, if data is logged at 2 minute intervals by wearable device WD1 for wearer W and a group of data records indicate that WD1 (and presumably wearer W) is at or near a location L1, then an immediate change in location to L2, where L1 and L2 are distant (e.g., 100 kilometers or more apart) may indicate an error in the location data, and so indicate that any other data in data record(s) associated with location L2 are unverified.

Additionally, if records of data log controls are part of the log, and the data log controls indicate data of type T1 from wearable device WD1 is restricted from logging, subsequent data of type T1 from wearable device WD1 can be determined to be unverified as being associated with wearer W.

Queries can apply to data items and/or provenance fields. Such queries can be made for an individual biological entity and made over populations of biological entities; e.g., a population of wearers of wearable devices. For example, a query could request a number of biological entities in the population, and a number of biological entities in the population whose pulse rate values had been lower than (or higher than) a predetermined value; e.g., 45 (or 150) beats per minute. Then, a ratio of biological entities whose pulse rate had been relatively low (or high) can be determined. Another query can request data from part or all of the population based on provenance data; e.g., some or all data records storing data received during a predetermined time interval, some or all data items whose size is larger (or smaller) than a predetermined value, etc. Queries can also use combinations of values of data items and values of provenance fields; e.g., all data records from device D1 on a specified Tuesday with glucose blood analyte data values that are equal to a predetermined value or predetermined range of values.

Queries over populations can be then be used to generate trend information. For example, if a location LE is suspected of being linked to a disease epidemic over a time range T1 to T2, then a query over one or more populations can provide information about who was at location LE during the T1 to T2 time range. Subsequent data records from those persons can provide trends of physiological data that may or may not be consistent with the disease. If trends in the subsequent data records indicate that people who were at location LE during the T1 to T2 time range had an increase likelihood of being afflicted with the disease, then conditions at location LE can be investigated to find a source and/or other information about the disease epidemic.

Trends can be detected over populations for general health issues as well. For example, data from populations of biological entities afflicted with a health condition HC can be studied to see if there are trends in the data before any symptoms of HC are presented; e.g., a relatively-high number of people in the HC-afflicted population have extreme values of a blood analyte in advance of the presentation of HC symptoms. Many other trends can be determined based on queries and query results from logged data.

In some cases, data can be logged for an extended duration of time; e.g., 50 years or longer. In particular, data can be logged for a time longer than the lifespan of a biological entity. The data can be logged to enable generational studies of physiological and/or other data, to generate long-term trend information, for other historical studies, and/or for other purposes. Over the extended duration of time, technology may lead to different techniques of storing, logging, and formatting data that can lead to uses of multiple formats of data being received and logged at the same time.

FIG. 13 depicts scenario 1300 for data retrieval, in accordance with an example embodiment. In scenario 1300, three applications 1310, 1312, and 1314 are each requesting data from BEDS device 740. Scenario 1300 begins with application 1310 generating and sending ReqData request 1320 to BEDS device 740 to request data about a biological entity identified as ID1; e.g., ID1 stores a name of the biological entity, where the data requested is "AllData" for the "3_Days", that is, all stored data related to the identified biological entity stored for the last three days, as indicated by ReqData request 1320. Upon reception of request 1320, BEDS device 740 can determine that request 1320 requires authorization before any data can be provided, but does not provide any authorization information. Thus, BEDS device 740 can determine that request 1320 should be denied. In scenario 1300, BEDS device 740 sends SendData message 1322 in response to request 1320 with a "NOT_AUTH" parameter to indicate to application 1310 that request 1320 is unauthorized and so is denied.

After receiving SendData message 1322, application 1310 can obtain appropriate authorization information; e.g., authentication and/or other identifying data related to a person or entity authorized to obtain data about the biological entity identified as ID1. After obtaining the authorization information, application 1310 can generate ReqData request 1324 with the same parameters as ReqData request 1324 plus authorization information "Auth1". Upon reception of request 1324, BEDS device 740 can determine that request 1324 includes Auth1, which is appropriate authorization information to provide the requested data, and so can determine that request 1324 should be honored. In scenario 1300, BEDS device 740 sends SendData message 1326 to application 1310 in response to request 1324 with data "Data1" with the requested data about ID1. In some scenarios, BEDS device 740 can use multiple messages to provide the requested data about ID1 to application 1310.

Scenario 1300 continues with application 1312 generating and sending ReqData request 1330 to BEDS device 740. As shown in FIG. 13, ReqData request 1330 can be used to request anonymized data using parameter "Anon", where the data is cardiological data as indicated using parameter "CardioData" for the last 7 days using the "7_Days" parameter for all biological entities as indicated using the "ALL" parameter with authorization information in an "Auth2" parameter.

Anonymized data can include data without identification information and/or with scrambled identification information; e.g., a heart rate without information that directly or indirectly indicates whose/which biological entity's heart was measured to obtain the heart rate. Anonymized data can include other non-identifying information about the biological entity; e.g., age, gender, height and/or weight data. Anonymized data can include only data allowed to be provided; i.e., a biological entity can opt out from (or opt in for) providing data about the biological entity, including but not limited to providing anonymized data.

In other scenarios, requests for anonymized data can include additional information about a population used to provide anonymized data; e.g., ages/age ranges, weight/ weight ranges, height/height ranges, gender, physiological condition information (e.g., persons who had (or did not have) a cardiac event in the last year, persons who smoke (or do not smoke), persons who have (or do not have) diabetes, persons who have (or do not have) a history of epilepsy, etc.), and/or other information to select anonymized data.

In scenario 1300, the authorization information in Auth2 of request 1330 allows access to anonymized cardiological data, and so BEDS device 740 determines to honor request 1330. Then, BEDS device 740 sends SendData message 1332 in response to request 1330 to provide application 1312 with data "Data2", where Data2 includes with the requested anonymized cardiological data. In some scenarios, BEDS device 740 can use multiple messages to provide the requested anonymized cardiological data to application 1312.

After reception of SendData message 1332, application 1312 generates and sends ReqData request 1334. As shown in FIG. 13, ReqData request 1334 can be used to request anonymized nutrition data as indicated using parameters "Anon" and "NutritionData" for the last 7 days using the "7_Days" parameter for all biological entities as indicated using the "ALL" parameter with authorization information in an "Auth2" parameter. In scenario 1300, the authorization information in Auth2 of request 1334 does not allow access to any nutrition data, and so BEDS device 740 determines to deny request 1334. In scenario 1300, BEDS device 740 sends SendData message 1336 in response to request 1334 with a "NOT_AUTH" parameter to indicate to application 1312 that request 1334 is unauthorized and so is denied.

Scenario 1300 continues with application 1314 generating and sending ReqData request 1340 to BEDS device 740. As shown in FIG. 13, ReqData request 1340 can be used to request anonymized data using parameter "Anon", where the data is nutrition data as indicated using parameter "NutritionData" for the month or more using the "MonthPlus" parameter for at least 500 biological entities as indicated using the "500" parameter with authorization information in an "Auth3" parameter.

In scenario 1300, the authorization information in Auth3 of request 1340 allows some access to anonymized nutrition data, and so BEDS device 740 determines to honor request 1340. Then, BEDS device 740 sends SendData message 1342 in response to request 1340 to provide application 1314 with data "Data3", where Data3 includes with the requested anonymized nutrition data. In some scenarios, BEDS device 740 can use multiple messages to provide the requested anonymized nutrition data about 500 (or more) biological entities to application 1312. In some cases, the 500 biological entities all can be different, while in other cases, data from one time period (e.g., a day, a week, a month) can be considered to be one unit of requested data, and so data from multiple time periods from the same biological entity can serve as multiple units of requested data.

Scenario 1300 continues with application 1314 generating and sending ReqData request 1344 to BEDS device 740. As shown in FIG. 13, ReqData request 1344 is the same as ReqData request 1340, and can be used to request anonymized nutrition data using parameter for another at least 500 biological with authorization information in an "Auth3" parameter. In scenario 1300, the authorization information in Auth3 of request 1344 allows some access to anonymized nutrition data, and so BEDS device 740 determines to honor request 1344. Then, BEDS device 740 sends SendData message 1346 in response to request 1344 to provide application 1314 with data "Data4", where Data4 includes with the requested anonymized nutrition data. In some scenarios, BEDS device 740 can use multiple messages to provide the requested anonymized nutrition data about 500 (or more) biological entities to application 1312.

Scenario 1300 continues with application 1314 generating and sending ReqData request 1348 to BEDS device 740. As shown in FIG. 13, ReqData request 1348 is the same as ReqData requests 1340 and 1344, and can be used to request anonymized nutrition data using parameter for another at least 500 biological entities with authorization information in an "Auth3" parameter. In scenario 1300, the authorization information in Auth3 of request 1344 allows some access to anonymized nutrition data, but that limited access does allow accessing data for an additional 500 biological entities. Therefore, BEDS device 740 determines to deny request 1348.

Then, BEDS device 740 sends SendData message 1350 in response to request 1348 to provide application 1314 with an "EXCEEDED_LIMIT" parameter to indicate that request 1348 exceeded the limited access provided by the authorization information indicated by the "Auth3" parameter. After BEDS device sends SendData message 1350, scenario 1300 can be completed.

Figure 14:
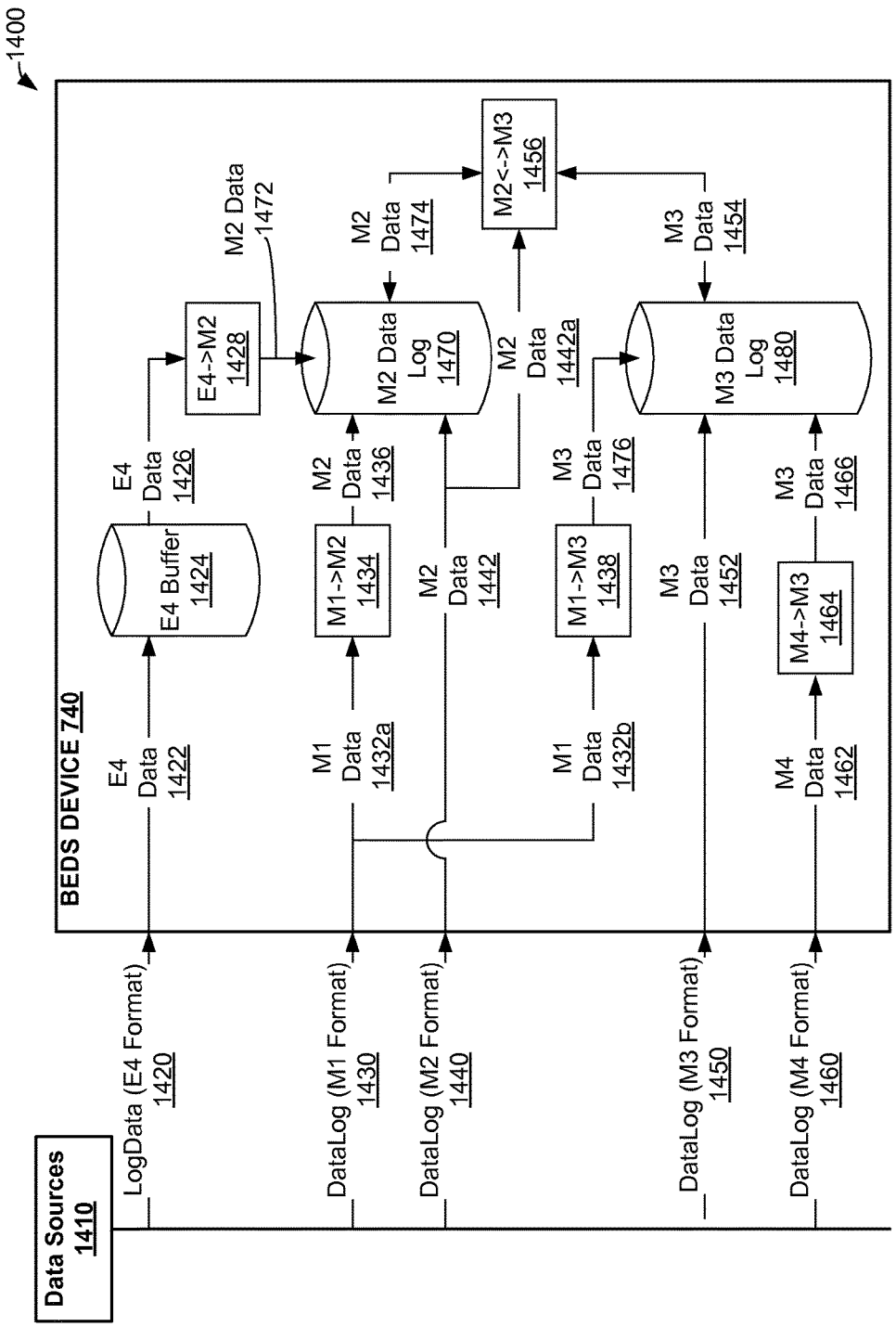
FIG. 14 depicts an example scenario for receiving and logging data of various data formats, in accordance with an example embodiment.

FIG. 14 depicts scenario 1400 for receiving and logging data of various data formats. In scenario 1400, data is received at BEDS device 740 in five different formats: data received in E4-formatted LogData messages 1420, M1-formatted LogData messages 1430, M2-formatted LogData messages 1440, M3-formatted LogData messages 1450, and M4-formatted LogData messages 1460. E4-formatted LogData messages 1420 use an E4 message format based on the English system of measurement, while each of M1-, M2-, M3-, and M4-formatted messages use a respective format based on the metric system of measurement. For example, M1-formatted messages 1430 use an M1 message format. For example, each of the E4, M1, M2, M3, and M4 message formats can be a variation of data format 1100 discussed above in the context of FIG. 11.

In scenario 1400, each of the E4, M1, M2, and M3 message formats was or is a standard message format used for logging data over several years, and the E4 and M1 formats have been superseded by current M2 and M3 standard formats. In scenario 1400, the M4 format is a message format under development for eventual use as a standard data logging format.

Data in the superseded formats E4 and M1 are processed in similar fashions by BEDS device 740. For example, when an E4-formatted message of the E4-formatted messages 1420 is received, E4-formatted data 1422 is extracted from the E4-formatted message and saved to E4 buffer 1424. E4-formatted data 1422 is saved as it takes a relatively long time to convert data in the superseded E4 format to a current standard M2 format via E4 to M2 conversion 1428. Thus, BEDS device 740 buffers E4-formatted data 1422 and converts the buffered E4-formatted data when resources are available for the conversion. After E4 to M2 conversion 1428 takes place, the converted E4-formatted data, now represented as M2 data 1472, can be logged along with other M2-formatted data in M2 data log 1470.

When an M1-formatted message of the M1-formatted messages 1430 is received, M1-formatted data 1432a is extracted from the M1-formatted message and converted in real-time to current standard M2 format via M1 to M2 conversion 1434. After M1 to M2 conversion 1434 takes place, the converted M1-formatted data, now represented as M2 data 1436, can be logged along with other M2-formatted data in M2 data log 1470. M1 data can also be converted to M3 formatted data as well, or instead of, being converted to M2 format; e.g., M1-formatted data 1432b is extracted from the M1-formatted message and converted in real-time to M3 format via M1 to M2 conversion 1438 and logged as M3 data 1476 in M3 data log 1480.

In scenario 1400, BEDS device 740 can store log data for long-term storage in either M2 or M3 formats in respective data logs 1470 and 1480, with a preference being shown to store data in the newer M3 format. Bi-directional conversion 1456 between M2 and M3 formats can be utilized to aid in balancing storage used between M2 data log 1470 and M3 data log 1480.

When an M2-formatted message of the M2-formatted messages 1440 is received, M2-formatted data 1442 is extracted from the M2-formatted message and is either logged directly into M2 data log 1470 or converted as M2-formatted data 1442a in real-time to the M3 format and logged as M3-formatted data 1454 in M3 data log 1480.

When an M3-formatted message of the M3-formatted messages 1450 is received, M3-formatted data 1452 is extracted from the M3-formatted message and is logged directly into M3 data log 1480. If data is to be converted from M3 format to M2 format, M3-formatted data 1454 is converted as M2formatted data 1474 using bi-directional conversion 1456 between M2 and M3 formats. Then, the resulting M2-formatted data 1474 can be logged in M2 data log 1470.

When an M4-formatted message of the M4-formatted messages 1460 is received, M4-formatted data 1462 is extracted from the M4-formatted message and converted in real-time to M3 format via M4 to M3 conversion 1434. The resulting M3 data, shown in FIG. 14 as M3 data 1466 is logged directly into M3 data log 1480.

At a later date, the M4 data format may be adopted as a standard data format. At that time, BEDS device 740 can be configured to store only M3-formatted and M4-formatted data. Then, M2data in M2 data log 1470 can be converted to M3 format using bi-directional conversion 1456 (and/or converted to M4 format using an M2->M4 conversion not shown in FIG. 14). Then, after the M4 data format is adopted, data received in M2 format can be converted to M3 (and/or M4) format before being stored in a data log of BEDS device 740.

Figure 15:
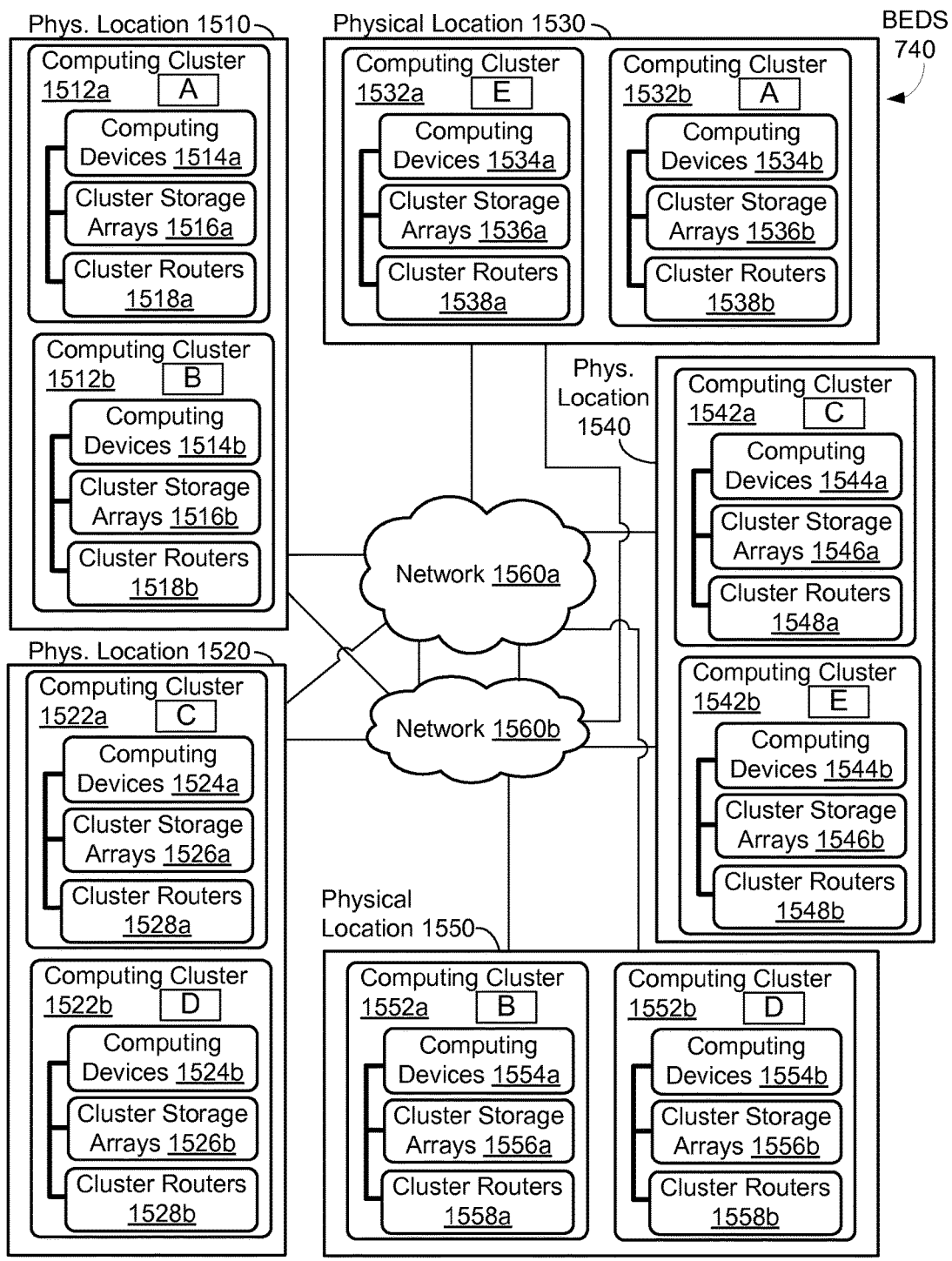
FIG. 15 depicts an example networked BEDS device, in accordance with an example embodiment.

FIG. 15 depicts example networked BEDS device 740, in accordance with an example embodiment. As shown in FIG. 15, BEDS device 740 can include computing clusters located in five different physical locations 1510, 1520, 1530, 1540, 1550, where each location is connected to each other using redundant networks 1560a, 1560b. A physical location can be part or all of a building; e.g., part or all of a room or floor of a building. That is, some or all of the physical locations can be within a common building or other structure. In other examples, some or all of physical locations 1510-1550 can be distinct; that is, the physical locations can be in separate buildings, cities/towns, states/provinces, countries, and/or on two or more different continents. Each of networks 1560a, 1560b can have some or all of the features discussed above for network 720 in the context of FIGS. 7 and 8B.

Each location of FIG. 15 includes two computing clusters—each computing cluster depicted in FIG. 15 includes one or more computing devices, cluster storage arrays, and cluster routers. Each of the respective computing clusters, computing devices, cluster storage arrays, and cluster routers can have some or all of the features of the respective devices described above as computing devices 800, 850a, 850b, 850c, computing clusters 859a, 859b, 859c, cluster storage arrays 860a, 860b, 860c, and cluster routers 861a, 861b, 861c discussed above in the context of FIGS. 8A and 8B.

For example, FIG. 15 shows that physical location 1510 includes two computing clusters 1512a, 1512b—each of computing clusters 1512a, 1512b can include some or all of the features of computing clusters 859a, 859b, 859c discussed above in the context of FIG. 8B. FIG. 15 indicates that computing clusters 1512a, 1512b respectively include: (a) computing devices 1514a, 1514b, which can include some or all of the features of computing devices 800, 850a, 850b, 850c discussed above in the context of FIGS. 8A and 8B; (b) cluster storage arrays 1516a, 1516b, which can include some or all of the features of cluster storage arrays 860a, 860b, 860c discussed above in the context of FIG. 8B; and (c) cluster routers 1518a, 1518b, which can include some or all of the features of cluster routers 861a, 861b, 861c discussed above in the context of FIG. 8B. Location 1510 is shown separately connected to each of networks 1560a and 1560b to indicate that each of computing clusters 1512a, 1512b in location 1510 is separately connected to each of networks 1560a and 1560b. FIG. 15 also shows that each of locations 1520, 1530, 1540, and 1550 are similarly configured with two computing clusters and separate links to networks 1560a, 1560b as described for location 1510.

In other examples, more or less than five locations can be used to store computing and other device(s) used for BEDS device 740. In still other examples, some or all of the locations used to store computing and other device(s) used for BEDS device 740 can have other than two computing clusters; that is, one or more computing devices not in a computing cluster, one computing cluster, or more than two computing clusters. In some of these still other examples, different locations can have different numbers of computing devices/computing clusters, while in other of these still other examples, some or all locations can each have the same number of computing clusters. Other examples are possible as well.

For BEDS device 740 shown in FIG. 15, data stored in the BEDS device is divided into five logical portions, labeled using letters A, B, C, D, and E. In other examples, stored in the BEDS device can be divided into one, two, three, four, or more than five logical portions. In the BEDS device 740 shown in FIG. 15, each logical portion of data is stored in two separate locations, which in other examples, logical portions of data can be stored in one location only, or more than two locations. In still other examples, some logical portions of data can be stored in more (or fewer) locations than other logical portions of data; e.g., logical portion A could be stored in four locations, logical portions B, C, and D could each be stored in three locations, and logical portion E could be stored in one location. Many other examples of apportioning data and storing the data in different locations are possible as well.

Each computing cluster 1512a, 1512b, 1522a, 1522b, 1532a, 1532b, 1542a, 1542b, 1552a, and 1552b is shown labeled with a letter "A", "B", "C", "D", and "E". The letter labeling each computing cluster indicates a corresponding logical portion of data stored on that computing cluster; e.g., computing cluster 1532a at location 1530 stores the logical portion of data labeled E, while computing cluster 1532b at location 1530 stores the logical portion of data labeled A.

Each location in FIG. 15 used two computing clusters to store a different pair of logical portions of data: location 1510 stores logical portion pair (A, B) on respective computing clusters 1512a, 1512b, location 1520 stores logical portion pair (C, D) on respective computing clusters 1522a, 1522b, location 1530 stores logical portion pair (E, A) on respective computing clusters 1532a, 1532b, location 1540 stores logical portion pair (C, E) on respective computing clusters 1542a, 1542b, and location 1550 stores logical portion pair (B, D) on respective computing clusters 1552a, 1552b.

In the example shown in FIG. 15, computing clusters are selected for storage by: first converting letters used to label logical portions of data to respective numbers: A=1, B=2, C=3, D=4, and E=5. The letters are traversed first by counting by one: A, B, C, D, E and then by counting by two (with wraparound from E back to B): A, C, E, B, and D, to obtain a list of characters: A B C D E A C E B D. Then, the first two logical portions of data referenced by the list—A B—are stored on the two computing clusters of first location 1510, the next two portions referenced in the list—C D—are stored on the two computing clusters of second location 1520, and so on until the last two portions referenced in the list—B D are stored on the two computing clusters of fifth location 1550.

If any single computing cluster is inaccessible or shut down for any reason, there is at least one other computing cluster that redundantly stores the same portion of data as the inaccessible/shut down computing cluster and so can be used to access that data; e.g., logical portion A is stored on computing clusters 1512a and 1532b. Further, if any one location is inaccessible or shut down for any reason, all five portions of data in the example shown in FIG. 15 can be accessed using the computing clusters in the remaining four locations. Further, networks 1560a, 1560b can be configured so that if either network 1560a or 1560b is inaccessible or shut down for any reason, the other network can convey all data communications used by BEDS device 740 as shown in FIG. 15. Therefore, as shown in FIG. 15, BEDS device 740 can be configured so that no single point of failure (computing cluster, network, or location of computing clusters) will cause complete loss of access to any logical portion of data stored using BEDS device 740. Many other techniques for apportioning data to computing and/or storage devices are possible as well.

Where example embodiments involve information related to a person or a device of a person, some embodiments may include privacy controls. Such privacy controls may include, at least, anonymization of device identifiers, transparency and user controls, including functionality that would enable users to modify or delete information relating to the user's use of a product.

Further, in situations in where embodiments discussed herein collect personal information about users, or may make use of personal information, the users may be provided with an opportunity to control whether programs or features collect user information (e.g., information about a user's physiology, medical history, social network, social actions or activities, profession, a user's preferences, or a user's current location), or to control whether and/or how to receive content from the content server that may be more relevant to the user. In addition, certain data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined. Thus, the user may have control over how information is collected about the user and used by a content server.

The above detailed description describes various features and functions of the disclosed systems, devices, and methods with reference to the accompanying figures. In the figures, similar symbols typically identify similar components, unless context dictates otherwise. The illustrative embodiments described in the detailed description, figures, and claims are not meant to be limiting. Other embodiments can be utilized, and other changes can be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

With respect to any or all of the ladder diagrams, scenarios, and flow charts in the figures and as discussed herein, each block and/or communication may represent a processing of information and/or a transmission of information in accordance with example embodiments. Alternative embodiments are included within the scope of these example embodiments. In these alternative embodiments, for example, functions described as blocks, transmissions, communications, requests, responses, and/or messages may be executed out of order from that shown or discussed, including substantially concurrent or in reverse order, depending on the functionality involved. Further, more or fewer blocks and/or functions may be used with any of the ladder diagrams, scenarios, and flow charts discussed herein, and these ladder diagrams, scenarios, and flow charts may be combined with one another, in part or in whole.

A block that represents a processing of information may correspond to circuitry that can be configured to perform the specific logical functions of a herein-described method or technique. Alternatively or additionally, a block that represents a processing of information may correspond to a module, a segment, or a portion of program code (including related data). The program code may include one or more instructions executable by a processor for implementing specific logical functions or actions in the method or technique. The program code and/or related data may be stored on any type of computer readable medium such as a storage device including a disk or hard drive or other storage medium.

The computer readable medium may also include non-transitory computer readable media such as non-transitory computer-readable media that stores data for short periods of time like register memory, processor cache, and random access memory (RAM). The computer readable media may also include non-transitory computer readable media that stores program code and/or data for longer periods of time, such as secondary or persistent long term storage, like read only memory (ROM), optical or magnetic disks, compact-disc read only memory (CD-ROM), for example. The computer readable media may also be any other volatile or non-volatile storage systems. A computer readable medium may be considered a computer readable storage medium, for example, or a tangible storage device.

Moreover, a block that represents one or more information transmissions may correspond to information transmissions between software and/or hardware modules in the same physical device. However, other information transmissions may be between software modules and/or hardware modules in different physical devices.

While various aspects and embodiments have been disclosed herein, other aspects and embodiments will be apparent to those skilled in the art. The various aspects and embodiments disclosed herein are for provided for explanatory purposes and are not intended to be limiting, with the true scope being indicated by the following claims.

What is claimed is:

1. A method, comprising:
receiving, at a computing device, a plurality of data items about a biological entity from a plurality of computing sources, wherein the plurality of computing sources comprises at least a wearable device being worn by the biological entity, and wherein the plurality of data items comprises a data item that includes physiological data obtained by one or more sensors of the wearable device;
verifying each data item of the plurality of data items using the computing device by at least:
determining a source of the data item from among the plurality of computing sources,
determining a provenance for the data item associated with the source of the data item, wherein the determined provenance is indicative of a timing of when the data item was generated, a location of where the data item was generated, or a characteristic of a sensor used to generate the data item,
determining that the wearable device is being worn by the biological entity based on the provenance for the data item, and
verifying that the data item is associated with the biological entity based at least on the determination that the wearable device is being worn by the biological entity;
after verifying that a particular data item of the plurality of data items is associated with the biological entity, storing the particular data item in a data log associated with the biological entity using the computing device, wherein storing the particular data item in the data log comprises storing a data record for the particular data item in the data log, and wherein the stored data record comprises (i) data about the biological entity associated with the particular data item, (ii) data about a time associated with the particular data item, and (iii) a type of activity associated with the particular data item;
receiving a request for a portion of data stored in the data log wherein the request is configured to indicate whether to include identifying information about biological entities associated with the requested portion of data; and
after determining that the request is configured to indicate not to include identifying information about biological entities associated with the requested portion of data, providing the requested portion of data stored in the data log without the identifying information about the associated biological entities.

2. The method of claim 1, wherein the physiological data comprises at least one of cardiac data, pulmonary data, or analyte data.

3. The method of claim 1, wherein storing the particular data item comprises storing the particular data item in two or more physical locations.

4. The method of claim 1, wherein the plurality of data items further comprises at least one of a data item about an environment of the biological entity, a data item about a mood of the biological entity, or a data item related to demographical information related to the biological entity.

5. A computing device, comprising:
a processor; and
a non-transitory computer readable medium configured to store at least a data log associated with a biological entity and executable instructions, wherein the executable instructions, when executed by the processor, cause the computing device to perform functions comprising:

receiving a plurality of data items about the biological entity from a plurality of computing sources, wherein the plurality of computing sources comprises at least a wearable device being worn by the biological entity, and wherein the plurality of data items comprises a data item that includes physiological data obtained by one or more sensors of the wearable device, verifying each data item of the plurality of data items by at least:

determining a source of the data item from among the plurality of computing sources, determining a provenance of the data item associated with the source, wherein the determined provenance is indicative of a timing of when the data item was generated, a location of where the data item was generated, or a characteristic of a sensor used to generate the data item, determining that the wearable device is being worn by the biological entity based on the provenance for the data item, and verifying that the data item is associated with the biological entity based at least on the determination that the wearable device is being worn by the biological entity, after verifying that a particular data item of the plurality of data items is associated with the biological entity, storing the particular data item in the data log associated with the biological entity, wherein storing the particular data item in the data log comprises storing a data record for the particular data item in the data log, and wherein the stored data record comprises (i) data about the biological entity associated with the particular data item (ii) data about a time associated with the particular data item, and (iii) a type of activity associated with the particular data item;

receiving a request for a portion of data stored in the data log, wherein the request is configured to indicate whether to include identifying information about biological entities associated with the requested portion of data; and after determining that the request is configured to indicate not to include identifying information about biological entities associated with the requested portion of data providing the requested portion of data stored in the data log without the identifying information about the associated biological entities.

6. The computing device of claim 5, wherein the physiological data comprises at least one of cardiac data, pulmonary data, or analyte data.

7. The computing device of claim 5, wherein storing the particular data item comprises storing the particular data item in two or more physical locations.

8. The computing device of claim 5, wherein the plurality of data items further comprises at least one of a data item about an environment of the biological entity, a data item about a mood of the biological entity, or a data item related to demographical information related to the biological entity.

9. A non-transitory computer readable medium configured to store at least executable instructions, wherein the executable instructions, when executed by a processor of a computing device, cause the computing device to perform functions comprising:

receiving a plurality of data items about a biological entity from a plurality of computing sources, wherein the plurality of computing sources comprises at least a wearable device being worn by the biological entity, and wherein the plurality of data items comprises a data item that includes physiological data obtained by one or more sensors of the wearable device;

verifying each data item of the plurality of data items by at least:

determining a source of the data item from among the plurality of computing sources, determining a provenance for the data item associated with the source of the data item, wherein the determined provenance is indicative of a timing of when the data item was generated, a location of where the data item was generated, or a characteristic of a sensor used to generate the data item, determining that the wearable device is being worn by the biological entity based on the provenance for the data item, and verifying that the data item is associated with the biological entity based at least on the determination that the wearable device is being worn by the biological entity;

after verifying that a particular data item of the plurality of data items is associated with the biological entity, storing the particular data item in a data log associated with the biological entity, wherein storing the particular data item in the data log comprises storing a data record for the particular data item in the data log and wherein the stored data record comprises (i) data about the biological entity associated with the particular data item, (ii) data about a time associated with the particular data item, and (iii) a type of activity associated with the particular data item;

receiving a request for a portion of data stored in the data log, wherein the request is configured to indicate whether to include identifying information about biological entities associated with the requested portion of data; and after determining that the request is configured to indicate not to include identifying information about biological entities associated with the requested portion of data, providing the requested portion of data stored in the data log without the identifying information about the associated biological entities.

10. The non-transitory computer readable medium of claim 9, wherein the physiological data comprises at least one of cardiac data, pulmonary data, or analyte data.

11. The non-transitory computer readable medium of claim 9, wherein the plurality of data items further comprises at least one of a data item about an environment of the biological entity, a data item about a mood of the biological entity, or a data item related to demographical information related to the biological entity.

12. The non-transitory computer readable medium of claim 9, wherein storing the particular data item comprises storing the particular data item in two or more physical locations.

* * * * *